(12) United States Patent
Ali

(10) Patent No.: US 11,969,527 B2
(45) Date of Patent: *Apr. 30, 2024

(54) DRUG-ELUTING BIOMATERIALS AND RELATED METHODS

(71) Applicant: BioSapien Inc., New York, NY (US)

(72) Inventor: Khatija Pinky Ali, Brooklyn, NY (US)

(73) Assignee: BioSapien Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/150,239

(22) Filed: Jan. 15, 2021

(65) Prior Publication Data

US 2021/0379251 A1 Dec. 9, 2021

Related U.S. Application Data

(63) Continuation of application No. 16/723,697, filed on Dec. 20, 2019, now Pat. No. 10,926,005.

(60) Provisional application No. 62/783,430, filed on Dec. 21, 2018.

(51) Int. Cl.
| | | |
|---|---|---|
| *A61L 31/14* | (2006.01) | |
| *A61K 31/513* | (2006.01) | |
| *A61K 31/7068* | (2006.01) | |
| *A61L 31/02* | (2006.01) | |
| *A61L 31/04* | (2006.01) | |
| *A61L 31/06* | (2006.01) | |
| *A61L 31/16* | (2006.01) | |

(52) U.S. Cl.
CPC .......... *A61L 31/146* (2013.01); *A61K 31/513* (2013.01); *A61K 31/7068* (2013.01); *A61L 31/026* (2013.01); *A61L 31/048* (2013.01); *A61L 31/06* (2013.01); *A61L 31/16* (2013.01); *A61L 2300/216* (2013.01); *A61L 2300/232* (2013.01); *A61L 2300/402* (2013.01); *A61L 2300/41* (2013.01); *A61L 2300/416* (2013.01)

(58) Field of Classification Search
CPC .............. A61L 31/14; A61L 2300/216; A61L 2300/16; B33Y 10/00; A61K 9/0024
See application file for complete search history.

(56) References Cited

U.S. PATENT DOCUMENTS

| | | | |
|---|---|---|---|
| 3,948,254 A | 4/1976 | Zaffaroni | |
| 5,487,897 A | 1/1996 | Polson et al. | |
| 10,926,005 B2* | 2/2021 | Ali | A61L 31/06 |
| 2005/0112397 A1* | 5/2005 | Rolfe | A61F 2/4455 |
| | | | 606/76 |

(Continued)

FOREIGN PATENT DOCUMENTS

| | | |
|---|---|---|
| CN | 1325291 A | 12/2001 |
| CN | 102319230 A | 1/2012 |

(Continued)

OTHER PUBLICATIONS

International Search Report and Written Opinion dated Mar. 25, 2020 for International Application Serial No. PCT/US2019/068056, (8 pages).

*Primary Examiner* — Carlos A Azpuru
(74) *Attorney, Agent, or Firm* — Wilson Sonsini Goodrich & Rosati

(57) ABSTRACT

Disclosed herein is a method of using a biomaterial for treating a condition. The biomaterial can comprise a plurality of geometric elements. Implantation of a biomaterial disclosed herein into a subject can treat, for example, cancer.

18 Claims, 6 Drawing Sheets

(56) References Cited

U.S. PATENT DOCUMENTS

| | | | |
|---|---|---|---|
| 2009/0264491 A1 | 10/2009 | McKay et al. | |
| 2011/0158963 A1 | 6/2011 | Font et al. | |
| 2014/0249643 A1 | 9/2014 | Jones et al. | |
| 2014/0324187 A1* | 10/2014 | Engqvist | A61B 17/8085 623/23.51 |
| 2016/0098495 A1* | 4/2016 | Dong | A61F 2/30942 219/76.12 |

FOREIGN PATENT DOCUMENTS

| | | |
|---|---|---|
| EP | 0649662 A1 | 4/1995 |
| WO | WO-2020132569 A1 | 6/2020 |

* cited by examiner

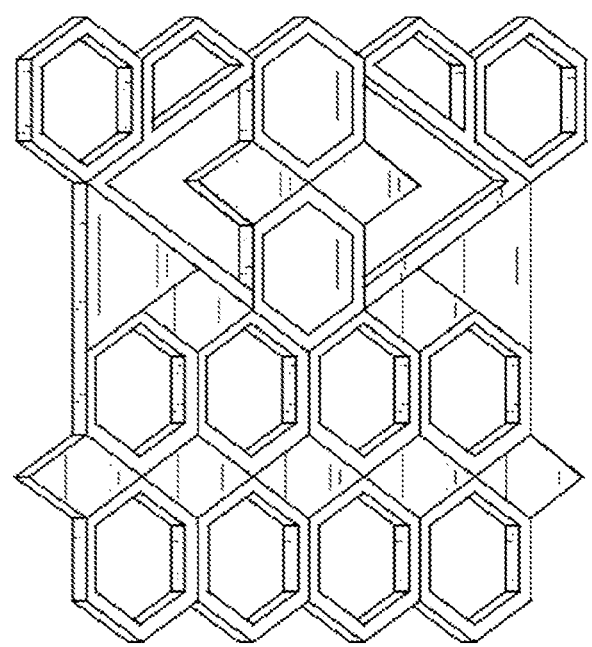
FIG. 2A
FIG. 2B

TRIPLE LAYER

DRUG-ELUTING BIOMATERIALS AND RELATED METHODS

CROSS-REFERENCE

This application is a continuation of U.S. patent application Ser. No. 16/723,697, which claims priority to U.S. Provisional Application No. 62/783,430 filed Dec. 21, 2018, each of which is incorporated herein by reference in its entirety.

BACKGROUND

Implantation of biomaterials can allow for the targeted delivery of a therapeutically-effective amount of a therapeutic agent. Targeted delivery of therapeutic agents can increase agent efficacy by increasing the exposure of target tissues to the agents and by mitigating systemic toxicity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

In some embodiments, the disclosure provides a biomaterial comprising a first plurality of geometric elements and a therapeutically-effective amount of a therapeutic agent, wherein a first geometric element of the first plurality of geometric elements is formed by a first porous border, wherein the first porous border comprises a polymer and the therapeutic agent, wherein a second geometric element of the first plurality of geometric elements is formed by a non-porous border and a first solid region comprising the polymer, wherein the therapeutic agent cannot diffuse into the second geometric element, wherein the first solid region is adjacent to and within the non-porous border, and wherein a portion of the first porous border is adjacent to a portion of the non-porous border.

In some embodiments, the disclosure provides a method of treating a condition, the method comprising: implanting a biomaterial into a subject, wherein the biomaterial comprises a first plurality of geometric elements and a therapeutically-effective amount of a therapeutic agent, wherein a first geometric element of the plurality of geometric elements is formed by a first porous border, wherein the first porous border comprises a polymer and the therapeutic agent, wherein a second geometric element of the first plurality of geometric elements is formed by a non-porous border and a first solid region comprising the polymer, wherein the therapeutic agent cannot diffuse into the second geometric element from the first porous border, wherein the first solid region is adjacent to and within the non-porous border, and wherein a portion of the first porous border is adjacent to a portion of the non-porous border.

BRIEF DESCRIPTION OF THE DRAWINGS

FIG. 2A and FIG. 2B show line drawings of a layer of a biomaterial of the disclosure.

DETAILED DESCRIPTION

Figure 1A:
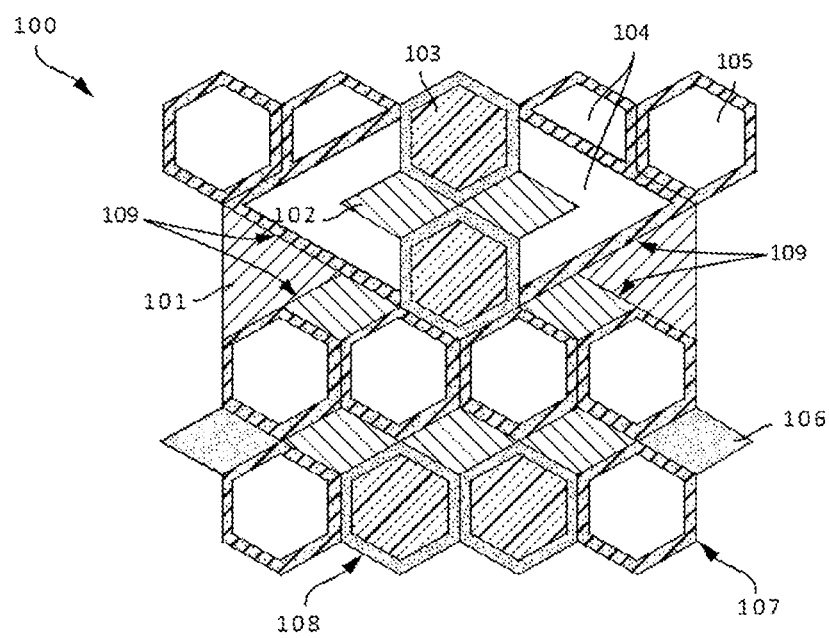
FIG. 1A is a line drawing showing the architecture of an example implementation of a single layer of a biomaterial of the disclosure.

Targeted delivery systems for therapeutic agents can increase the efficacy of a therapeutic agent by, for example, increasing exposure of target tissues to the therapeutic agent, and by mitigating systemic toxicity. Targeted delivery can be desirable in the context of therapies that are highly toxic when administered systemically, and/or when administered over a prolonged period of time, such as chemotherapeutic agents and opioids.

Advances in three-dimensional (3D) printing technologies can create new opportunities for producing customized delivery systems that can be adapted for a wide range of uses in the surgical theater. Three-dimensional printing can be advantageous due to the relatively low cost, simplicity, and versatility of a 3D printing system, as well as the high speed with which custom devices can be produced.

Disclosed herein is a biomaterial that can serve as a surgical article and/or drug delivery system that can release a therapeutic agent directly to a target site over prolonged periods of time. The biomaterial can comprise one or more therapeutic agents that are loaded into a geometric element or a plurality of geometric elements of the article. Biomaterials, such as surgical articles, can be adapted for in situ sustained release of the one or more therapeutic agents. In some embodiments, the surgical articles are printed using an extrusion 3D printing method. Biomaterials can be custom printed in a shape and size suitable to cover a target site in situ. Biomaterials for implantation in situ can be in the general form of a surgical tape or mesh that can also be folded and/or layered. Suitable target sites include any site in the body of a subject requiring treatment with the one or more therapeutic agents. Non-limiting examples of target sites include tissues such as a blood vessel, lymph nodes, cartilage, bone, liver, lungs, heart, pancreas, spleen, gastrointestinal tract, brain, pelvic, breast, and pulmonary tissue. In some embodiments, a biomaterial can be applied to deep tissue and connective tissues such as muscle and smooth muscles.

Biomaterials disclosed herein can comprise a polymer material, within at least a portion of which one or more therapeutic agents can be dispersed. In some embodiments, the polymer material can also contain one or more additives. The polymer material can comprise or consist of one or more bioresorbable and/or biodegradable polymers, or a mixture of polymers including at least one bioresorbable and/or biodegradable polymer.

In some implementations, the 3D printed surgical articles are sterile, sterilizable, and/or sterilized before implantation into a subject.

A biomaterial disclosed herein can be biocompatible. A biocompatible biomaterial can be administered or implanted into the body of a subject without undesirable effects such as, for example, an immune and/or inflammatory reaction.

A biomaterial disclosed herein can be biodegradable. A biodegradable biomaterial can degrade (partially or completely) under physiological conditions into non-toxic products that can be metabolized or excreted from the body. In some instances, biodegradable materials are degraded by enzymatic activity, for example by enzymatic hydrolysis.

In some embodiments, a biomaterial of the disclosure is bioresorbable or bioabsorbable. Bioresorbable or bioabsorbable materials can be broken down and absorbed by cells and/or tissues.

In some embodiments, a biomaterial described herein is configured to resorb and/or degrade after placement in situ over a period of time ranging from about 1 day to about 1 week, about 1 week to about 1 month, 1 month to about 3 months, about 3 months to about 6 months, about 6 months to about 12 months, about 12 months to about 24 months, or from about 2 years to about 5 years. The resorption and/or degradation time can be modulated by controlling the composition of the polymer material, including the types of polymers and porosity of the material, as well as by the two- and three-dimensional arrangement of geometric elements and comprising the article.

A surgical article as described here can comprise one geometric element or a plurality of geometric elements. In some embodiments, the geometric elements of a plurality of geometric elements are in fluid communication with each other. In some embodiments, a plurality of geometric elements is printed on an x-y plan, for example as a ribbon, grid, or other shape to form a biomaterial of a desired shape and/or size. In some embodiments, a plurality of geometric elements can be printed vertically, on top of one another. In some embodiments, a thickness of a single layer article can be in the range of about 0.1 cm to about 1 cm, about 0.25 to about 1 cm, about 0.5 to about 1 cm, about 0.75 to about 1 cm, about 0.1 cm to about 2 cm, about 0.25 to about 2 cm, about 0.5 to about 2 cm, about 0.75 to about 2 cm, about 0.1 cm to about 3 cm, about 0.25 to about 3 cm, about 0.5 to about 3 cm, about 0.75 to about 3 cm, about 0.1 cm to about 4 cm, about 0.25 to about 4 cm, about 0.5 to about 4 cm, about 0.75 to about 4 cm, about 0.1 cm to about 5 cm, about 0.25 to about 5 cm, about 0.5 to about 5 cm, or about 0.75 to about 5 cm.

In some embodiments, a biomaterial of the disclosure comprises multiple layers, wherein each layer comprises a plurality of geometric elements. For example, a biomaterial of the disclosure can comprise 1, 2, 3, 4, 5, 6, 7, 8, 9, 10, or more layers. In some embodiments, each layer of a biomaterial is oriented such that the layer is offset from the unit above and/or below, for example at a defined angle such as, for example, about 15 degrees, about 30 degrees, about 45 degrees, about 60 degrees, about 90 degrees, about 105 degrees, about 120 degrees, about 135 degrees, about 150 degrees, about 165 degrees, or about 180 degrees.

The overall dimensions of a biomaterial of the disclosure can be adapted to accommodate a wide range of in situ target sites. In accordance with any of these implementations, one or more geometric elements of a plurality of geometric elements can be printed with or without one or more therapeutic agents. A biomaterial of the disclosure can have any shape. For example, the overall shape of a surgical article in accordance with the present description can be circular, oval, rectangular, triangular, octangular, pentangular, hexangular, heptangular, or square, and the size can be adapted to cover an area in the range of, for example, from about 4 cm$^2$ to about 200 cm$^2$. In some embodiments, the article is of a size suitable to cover an area of from about 20 cm$^2$ to about 50 cm$^2$, from about 50 cm$^2$ to about 100 cm$^2$, or from about 100 cm$^2$ to about 200 cm$^2$. In some embodiments, the article can range in size from about 2 cm×about 2 cm up to about 12 cm×about 10 cm. For example, a biomaterial of the disclosure can be a 2 cm×2 cm, 4 cm×4 cm, 6 cm×6 cm, or 8 cm×8 cm square article, or 4 cm×6 cm, 8 cm×6 cm, 10 cm×8 cm, or 12 cm×10 cm rectangular article.

In some embodiments, a biomaterial of the disclosure (e.g. a surgical article) can further comprise a loop or similar feature configured to facilitate the placement of the biomaterial in situ, for example by suturing.

Structure of Geometric Elements.

A biomaterial of the disclosure can comprise a plurality of geometric elements. Geometric elements of a plurality of geometric elements can be adjacent and/or in fluidic communication with one another. In some embodiments, the geometric elements form a layer. Geometric elements can be formed by a border comprising a polymer. In some embodiments, a border of a geometric element can further comprise one or more therapeutic agents disclosed herein. A border forming a geometric element can be porous, non-porous, or minimally porous. A porous border can allow for the diffusion of a therapeutic agent through the border and into or out of the geometric element formed by the border. In some embodiments, a border is minimally porous such that a therapeutic agent cannot diffuse through the border and into the geometric element formed by the border.

A geometric element formed by a border can comprise, for example, an empty space or a solid region within the border. A solid region of a geometric element can be porous, non-porous, or minimally porous. A porous solid region can allow for the diffusion of a therapeutic agent through the solid region and into or out of a geometric element. In some embodiments, a solid region is minimally porous such that a therapeutic agent cannot diffuse through the solid region and into the geometric element formed by the border.

A border and/or solid region of a geometric element can have a degree of porosity. In some embodiments, the degree of porosity of a border or solid region is about 10% to about 99%. In some embodiments, the degree of porosity of a border or solid region is about 10% to about 20%, about 10% to about 30%, about 10% to about 40%, about 10% to about 50%, about 10% to about 60%, about 10% to about 70%, about 10% to about 80%, about 10% to about 90%, about 10% to about 99%, about 20% to about 30%, about 20% to about 40%, about 20% to about 50%, about 20% to about 60%, about 20% to about 70%, about 20% to about 80%, about 20% to about 90%, about 20% to about 99%, about 30% to about 40%, about 30% to about 50%, about 30% to about 60%, about 30% to about 70%, about 30% to about 80%, about 30% to about 90%, about 30% to about 99%, about 40% to about 50%, about 40% to about 60%, about 40% to about 70%, about 40% to about 80%, about 40% to about 90%, about 40% to about 99%, about 50% to about 60%, about 50% to about 70%, about 50% to about 80%, about 50% to about 90%, about 50% to about 99%, about 60% to about 70%, about 60% to about 80%, about 60% to about 90%, about 60% to about 99%, about 70% to about 80%, about 70% to about 90%, about 70% to about 99%, about 80% to about 90%, about 80% to about 99%, or about 90% to about 99%. In some embodiments, the degree of porosity of a border or solid region is about 10%, about 20%, about 30%, about 40%, about 50%, about 60%, about 70%, about 80%, about 90%, or about 99%. In some embodiments, the degree of porosity of a border or solid region is at least about 10%, at least about 20%, at least about 30%, at least about 40%, at least about 50%, at least about 60%, at least about 70%, at least about 80%, or at least about 90%. In some embodiments, the degree of porosity of a border or solid region is at most about 20%, at most about 30%, at most about 40%, at most about 50%, at most about 60%, at most about 70%, at most about 80%, at most about 90%, or at most about 99%.

The porosity of borders and/or solid regions can vary throughout a biomaterial of the disclosure. In some embodiments, a porous border surrounds a solid region that is minimally porous or non-porous. In some embodiments, a minimally porous or non-porous border surrounds a solid region that is porous. In some embodiments, a non-porous or minimally porous border surrounds a solid region that is non-porous or minimally porous. In some embodiments, a porous border surrounds a porous solid region.

Adjacent geometric elements can share an edge, and thus form a portion of the border forming the geometric elements. In some embodiments, adjacent elements each comprise distinct edges/borders that are adjacent to and/or in contact with one another.

Borders can form geometric elements of any shape. For example, a border can form a geometric element that is circular, elliptical, triangular, rectangular, pentangular, hexangular, heptangular, octangular, or irregularly shaped. In some embodiments, a border forms a geometric element that is a nonagon or decagon. Geometric elements of a plurality of geometric elements can be the same or different shapes. In some embodiments, a biomaterial or layer thereof can comprise a plurality of geometric elements defining two or more hexagons, triangles, and diamonds, or portions thereof. In some implementations, the length of the edges of a particular element may range from 1.0 mm to 10 mm, or from 1.0 mm to 5 mm, or from 1.0 mm to 3 mm. It is understood that, depending on the geometric shape defined by the edges of the element, the edges may be the same or different lengths. In some embodiments, each edge of a geometric element is uniform in length and/or width.

In some embodiment, a biomaterial disclosed herein is comprised of a plurality of layers, each layer formed from a plurality of open and filled geometric elements forming a defined pattern. The plurality of geometric elements can comprise elements having three, four, five, or six edges. In some embodiments, the edges of the elements can define one or more geometric shapes selected from triangles, diamonds, hexagons, and portions of any of the foregoing. In some embodiments, the triangles are equilateral triangles and the edges of each geometric element are of uniform length. In some embodiments, the edges have a length of from about 1 to about 3 mm, from about 1 to about 2 mm, for example about 1.0 mm, about 1.5 mm, about 2.0 mm, about 2.5 mm, or about 3.0 mm.

One or more therapeutic agents can be loaded into geometric elements. For example, one or more geometric agents can be dispersed within a solid region or a border of a one or more geometric elements of a biomaterial of the disclosure.

Arrangement of Geometric Elements.

In some embodiments, a plurality of geometric elements forming a biomaterial or layer thereof here is arranged in a defined pattern of elements comprising solid regions (i.e., filled elements) and empty spaces (i.e., open elements), the pattern adapted to modulate release of the therapeutic agent(s) from the drug reservoir element(s) of the unit article in situ. For example, the size and shape of the elements forming the biomaterial or layer thereof can be increased or decreased to modulate the surface area of the filled elements and the pore size of the open elements, in order to modulate the release of the therapeutic agent or agents from the article. The volume and number of therapeutic-agent loaded element(s) can determine the amount of the therapeutic agent(s) in the unit article and the amount released in situ at the target site. The volume of the therapeutic-agent loaded element(s) can be increased, for example, by printing multiple single layers of biomaterial on top of each other until a desired thickness is reached, thereby allowing a higher loading volume for the therapeutic agent(s). The defined pattern of open and filled geometric elements can further be used to modulate the total surface area of the unit article, as well as the surface area of the unit article from which a therapeutic agent(s) is released.

Release of Therapeutic Agents.

Release of one or more therapeutic agents into a target site in situ from a biomaterial of the disclosure can occur from the exposed surface(s) of the biomaterial. Additionally, or alternatively, one or more therapeutic agents can diffuse within a biomaterial disclosed herein.

For example, in some embodiments, a defined pattern of open and filled geometric elements with porous and/or non-porous components (e.g. borders or solid regions) can be used to direct or focus any intra-biomaterial diffusion of a therapeutic agent to a defined region of the biomaterial. Focusing diffusion of a therapeutic agent can have the effect of a more concentrated release of a therapeutic agent from a region of a biomaterial. Thus, depending on the type of therapy, duration of treatment, and the location of an in situ target site, the amount and rate of release of therapeutic agent(s) from a biomaterial described herein can be controlled through a combination of the defined pattern of open and filled geometric elements forming the biomaterial, the inclusion of one or more additives, such as a poragen, and the amount of the agent(s) loaded into the geometric elements of the biomaterial.

In some embodiments, release of a therapeutic agent from a biomaterial disclosed herein can be modulated by increasing the thickness of the biomaterial (e.g. by using multiple layers) as well as by sequestering the geometric element(s) loaded with therapeutic agent within internal layers of a folded biomaterial or a stack of biomaterials or layers thereof. Folding and stacking of the biomaterials of layers thereof in this manner can reduce the surface area from which a therapeutic agent can be released. In some embodiments, a surgical article can be formed from alternating layers of unit articles in a stacked configuration where the alternating layers are staggered or slanted, for example at about 180 degrees, about 90 degrees or about 45 degrees. For example, in the staggered configuration, two or more layers of a biomaterial are layered horizontally on top of one another at a 180 degree, 90 degree, or 45 degree angle. In some embodiments, the thickness of a folded or stacked article can range from about 0.5 cm to about 3 cm. In some embodiments, the thickness of the folded or stacked article is about 0.5 cm, about 1.0 cm, about 1.5 cm, or about 2.0 cm.

In some embodiments, one or more therapeutic agents can be coated onto the surface of a biomaterial in addition to, or instead of, being dispersed within the polymer material of the biomaterial.

Biomaterial Structure.

A schematic of a non-limiting example of a biomaterial of the disclosure is shown in FIG. 1A. As shown in FIG. 1A, a biomaterial of the disclosure (100) can comprise twenty-seven open (i.e. filled with empty space) or filled elements defining five different geometric shapes and portions thereof. Two filled triangular elements (101) and seven filled diamond shaped elements (102) can be positioned to modulate diffusion of a therapeutic agent infused within portions of the biomaterial, including within adjacent filled hexagonal elements (103). In some embodiments, the filled elements each contain the same polymer or mixtures of polymers. The filled elements can contain polymers or mixtures of polymers with the same or different porosities. For example, some of the filled elements can function as a barrier to intra-material diffusion of the therapeutic agent, while other filled elements can contain pores that serve to allow intra-material diffusion of the therapeutic agent into the area defined by the porous filled elements. The degree of porosity of polymers making up the biomaterial can be modulated by the manufacturing process.

In FIG. 1A, the filled triangular elements (101) are formed by a non-porous border (109) around an essentially non-porous solid region. The filled triangular elements (109) can serve to focus the intra-material diffusion of the therapeutic agent into adjacent regions defined by porous or open elements, for example the filled hexagonal elements (103), the open hexagonal elements, (105), and/or the open triangular elements and portions thereof (104). The focusing of the intra-material diffusion can, for example, target release of a therapeutic agent toward a defined region of the biomaterial for release in a more concentrated fashion at a particular region within a target site in situ.

As shown in FIG. 1A, a biomaterial disclosed herein can comprise four filled hexagonal elements (103) formed by a porous border (108) and a solid region, each comprising polymer and the therapeutic agent dispersed within the polymer. The biomaterial can further comprise two filled diamond-shaped elements (106) formed by a solid region and a porous border, each comprising polymer and the therapeutic agent dispersed within the polymer. In some embodiments, the porous border is formed by the edges of the solid region. Throughout the biomaterial, the border of a geometric element with a solid region can have a composition that is the same or different than the composition of the solid region. In some embodiments, a biomaterial contains diamond-shaped filled elements (102) formed by a porous border and a porous solid region that is not infused with therapeutic agent, but which allows for intra-material diffusion of the therapeutic agent into these diamond-shaped filled elements (102). Diffusion of the therapeutic agent into the non-therapeutic agent infused diamond-shaped elements (102) increases the surface area from which the therapeutic agent diffuses into the in situ target site. A biomaterial disclosed herein can further comprise a plurality of filled and open elements that serve to increase the overall surface area of the biomaterial, impart structural integrity to the biomaterial, impart flexibility to the bio biomaterial, and/or serve as optional fixation points on the biomaterial. For example, as shown in FIG. 1A, open elements (104, 105) of a biomaterial disclosed herein can serve as fixation points to suture the biomaterial in place at a target site. The borders (107) forming the open elements (104, 105) can be porous or nonporous borders. In some embodiments the borders forming the open elements (104, 105) of a biomaterial disclosed herein comprise a polymer and a therapeutic agent (e.g. 5-fluorouracil) infused within the polymer.

Figure 3:
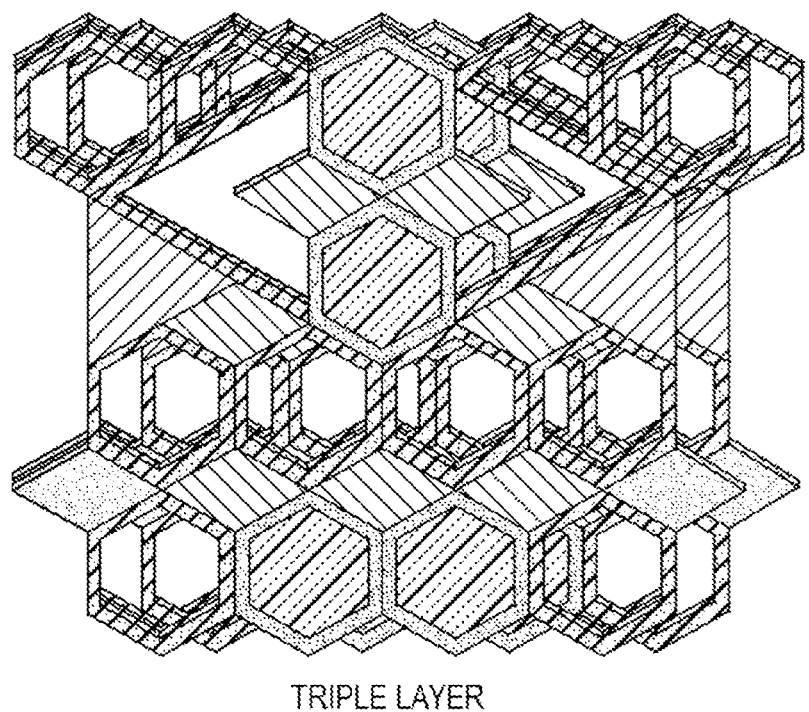
FIG. 3 shows a three-layered biomaterial comprising three layers of the single layer biomaterial described in FIG. 1A

A biomaterial disclosed herein can be one or multiple layers. For example, a biomaterial of the disclosure can be 1, 2, 3, 4, 5, 6, 7, 8, 9, 10, or more layers. A non-limiting example of a single layer biomaterial is shown in FIG. 2A and FIG. 2B. FIG. 2A shows a head-on view, while FIG. 2B and shows a rotated view of a single layer article. A non-limiting example of a multiple layer biomaterial is shown in FIG. 3. FIG. 3 depicts a layered biomaterial containing three layers of the biomaterial described in FIG. 1, with each layer offset by about 30 degrees.

Intra-Material Diffusion.

Figure 1B:
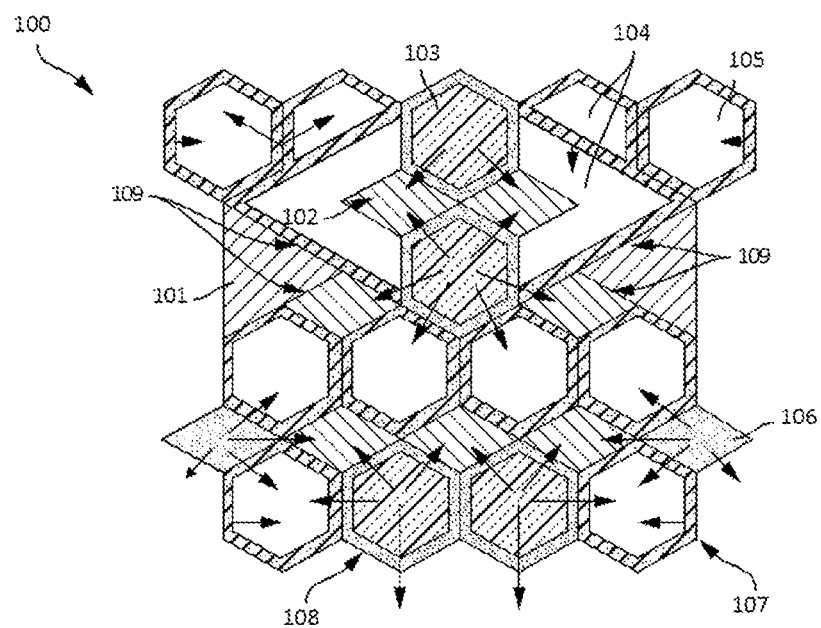
FIG. 1B shows a schematic representation of the intra-article diffusion of a therapeutic agent disclosed herein.

In some embodiments, a biomaterial disclosed herein modulates the diffusion of a therapeutic agent within and from the biomaterial. A non-limiting example of an intra-material diffusion pattern of a therapeutic agent through a biomaterial disclosed herein (the biomaterial depicted in FIG. 1A) is shown in FIG. 1B. In FIG. 1A and FIG. 1B, filled hexagonal elements (103) and diamond shaped elements (b) contain the bulk of the therapeutic agent per unit of the biomaterial, although the edges defining the elements also contain therapeutic agent. In some embodiments, the six filled hexagonal elements can contain a total of 50-500 mg, 100-400 mg, or 150-250 mg of the therapeutic agent. Each element can contain the same or a different amount of the therapeutic agent. In some embodiments, the therapeutic agent diffuses into the region defined by filled diamond-shaped elements (102), which have a degree of porosity that is conducive to such diffusion. In some embodiments, a biomaterial disclosed herein further comprises diamond-filled elements infused with a therapeutic agent (106) that serve as additional reservoirs of the therapeutic agent.

Polymers.

Biomaterials described herein can be formed from a 3D printed polymer material. In some embodiments, the polymer material can comprise bioresorbable and/or biodegradable polymers, or a mixture of polymers including one or more bioresorbable and/or biodegradable polymers. Suitable polymers include, but are not limited to, polycaprolactone (PCL), poly(lactic acid) (PLA), poly(lactic-co-glycolic acid), which may also be referred to interchangeably as poly(lactide-co-glycolide) (PLGA), poly(ethylene glycol) diacrylate (PEGDA) and poly(ester amide) copolymers (PEA).

In some embodiments, the polymer material comprises or consists of PCL. In some embodiments, the polymer material is a blend of PCL with one or more additional polymers. In some embodiments, the one or more additional polymers blended with the PCL is selected from PLA, PLGA, and PEGDA. In some embodiments, the one or more additional polymers blended with the PCL is selected from polyvinyl chloride and polyethlyene oxide (PEO), or from PEA, polyesters, poly(alpha-hydroxy acids), polylactones, polyorthoesters, polycarbonates, polyanhydrides, polyphosphazenes, or a gelatin based polymer such as poly(ethylene glycol) (PEG)-gelatin methacrylate.

In some embodiments, the polymer material is a blend of PCL and PLGA, for example a blend of 1:1 to 10:1 PCL: PLGA. In some embodiments, the polymer material comprises a 1:1-5:1 mixture of PCL/PLGA, a 1:1-2:1 mixture of PCL/PLGA. The ratio of lactide:glycolide of the PLGA may also be varied to modulate release of the therapeutic agent and degradation time of the article in situ. The percentage of PCL in the blend can determine the density of the co-polymer and the ratio of PCL to PLGA can indicate the number of elongated (stretched) polymer fibers present in the co-polymer. An increased number of elongated fibers throughout the polymeric article can allow greater drug release from the article. In some embodiments, the PLGA % weight ratio is from 50:50-90:10 lactide/glycolide. In some embodiments, the PLGA % weight ratio is 85:15 lactide/glycolide, 60:40 lactide/glycolide.

Modulation of the density and/or porosity of a polymer material can modulate the release of a therapeutic agent from a biomaterial. For example, release of a therapeutic agent can be increased by increasing the pore size and/or increasing the porosity of the polymer material. In some embodiments, the polymer material comprises or consists of PCL having micropores in the range of 50-250 microns in size, with an average size of about 80 microns. Blending the PCL with another polymer, such as PLA, PLGA, PEGDA, or PEO, yields larger pores, for example in the range of 200 to 800 microns. In some embodiments, a less porous polymer material can be used to slow release of a therapeutic agent. For example, a polymer material that comprises from about 60% to 100% PCL, or from 60-80% PCL, or from 80-100% PCL can be used.

In some embodiments, a biomaterial of the disclosure can comprise geometric elements that each comprise two or more different polymer materials. For example, the polymer material forming the element edges can differ from the polymer material forming the 'fill' of a filled element, and different filled elements can be filled with different polymer materials. The polymer materials can differ, for example, in the type of polymer or mixture of polymers making up the polymer material. Additionally, the polymer materials forming the different portions of geometric elements can have different densities and/or porosities and can also differ in the optional additives they contain. For example, a multi-head 3D printer can allow for different substances to be printed simultaneously. For example, each head can contain different components so one head can contain the polymer and therapeutic agent of choice and a second head can contain only polymer. As an STL file is converted into G-code, programmable code for the multi-head printer is created allowing the 3D printer to read which article segments contain PCL and which article segments contain PCL and drug (as programmed). Similarly, more than one drug can be printed at a time. For example, an analgesic (e.g., NSAID) can be printed simultaneously with a chemotherapy drug (e.g. 5-fluorouracil).

Additives.

In some embodiments a biomaterial of the disclosure, or portions thereof, can comprise one or more additives. Non-limiting examples of additives include a radiopaque agent, a colorant, an oil (e.g., silicone) and a porogen.

The density and/or porosity of the polymer material, and therefore the release of the therapeutic agent from the surgical article, can be modulated by including one or more additives, such as a porogen, in the polymer material. In some embodiments, the polymer material, or at least a portion of the polymer material, comprises a porogen. The term "porogen" refers to a material that diffuses, dissolves, and/or degrades leaving pores within the polymer material. In some embodiments, a 3D printed surgical article as described herein can be printed with at least a portion of polymer material comprising a porogen. Depending on the porogen used, the porogen can subsequently, either prior to implantation, or after implantation, diffuse, dissolve, and/or degrade, leaving behind pores in the surgical article. Non-limiting examples of porogens include, water soluble materials such as salts, polysaccharides, water soluble inorganic materials such as bioactive glass, silicate-based nanoparticles, such as lithium sodium magnesium silicate (Laponite™) and water soluble or physiologically labile natural or synthetic polymers, including for example, poly(vinylpyrrolidone), pullulan, poly(glycolide), poly(lactide), poly(lactide-co-glycolide), other polyesters, and starches.

In some embodiments, a porogen of the disclosure is a bioactive glass such as a ceramic within the Na—Ca—Si—P—O system. In embodiments, the bioactive glass comprises $SiO_2$ and CaO. In embodiments, the bioactive glass further comprises $Na_2O$ and $P_2O_5$. In some embodiments, the bioactive glass is selected from Bioglass®, bioactive glass 45S5 (45 wt % $SiO_2$, 24.5 wt % CaO, 24.5 wt % $Na_2O$ and 6.0 wt % $P_2O_5$), bioactive glass 58S, 60 wt % $SiO_2$, 36 wt % CaO and 4 wt % $P_2O_5$, bioactive glass 70S30C, 70 wt % $SiO_2$, and 30 wt % CaO, bioactive glass S53P4, 53 wt % $SiO_2$, 23 wt % $Na_2O$, 20 wt % CaO and 4 wt % $P_2O_5$ (anti-bacterial), and laponite $(Na^+_{0.7}(Si_8Mg_{5.5}Li_{0.3})O_{20}(OH)_4]^-$.

In some embodiments, a sacrificial or fugitive ink can be used to introduce pores or channels into a polymer material. Non-limiting examples of materials that can serve as fugitive inks include poloxamers, such as Pluronic™ F127, which consists of hydrophobic poly(propylene oxide) (PPO) and hydrophilic poly(ethylene oxide) (PEO) segments arranged in a PEO-PPO-PEO configuration.

Therapeutic Agents.

Biomaterials described here can comprise a therapeutically-effective amount of one or more therapeutic agents. In some embodiments, therapeutic agents are loaded into solid regions of geometric elements of the biomaterial. In some embodiments, the therapeutic agent(s) can be contained within the borders (e.g. a porous border) forming the edges of one or more geometric elements of the article.

In some embodiments, the one or more therapeutic agents may be selected from an anti-cancer agent, an antimicrobial agent, an antibiotic, a local anesthetic or analgesic, a statin, and an anti-inflammatory agent.

In some embodiments, the anti-cancer agent is selected from capecitabine, cisplatin, carboplatin, cyclophosphamide, docetaxel, doxorubicin, etoposide, fluorouracil, floxuridine, gemcitabine, ifosfamide, irinotecan, methotrexate, oxaliplatin, paclitaxel, pemetrexed, raltitrexed, regorafenib, vincristine, vinorelbine, and combinations thereof.

In some embodiments, the antimicrobial agent is an antibiotic. In some embodiments, the antibiotic can be a broad spectrum antibiotic, such as gentamicin, clindamycin, and erythromycin, or a gram positive and gram negative family antibiotic such as an ampicillin and a cephalosporin. Non-limiting examples of antibiotics suitable for the uses herein include penicillin V potassium, cloxacillin sodium, dicloxacillin sodium, oxacillin sodium, carbenicillin indanyl sodium, oxytetracycline, hydrochloride, tetracycline hydrochloride, clindamycin phosphate, clindamycin, hydrochloride, clindamycin palmitate HCL, lincomycin HCL, novobiocin sodium, nitrofurantoin sodium, and metronidazole hydrochloride.

In some embodiments, a therapeutic agent is a local anesthetic or analgesic. Non-limiting examples of local anesthetics or analgesics include lidocaine, bupivacaine, tetracaine, ropivacaine, benzocaine, and fentanyl, codeine hydrochloride, codeine phosphate, codeine sulphate, dextromoramide tartrate, hydrocodone bitartrate, hydromorphone hydrochloride, pethidine hydrochloride, methadone hydrochloride, morphine sulphate, morphine acetate, morphine lactate, morphine meconate, morphine nitrate, morphine monobasic phosphate, morphine tartrate, morphine valerate, morphine hydrobromide, morphine hydrochloride, and propoxyphene hydrochloride.

In some embodiments, a therapeutic agent is an anti-inflammatory agent. An anti-inflammatory agent can be selected from a non-steroidal anti-inflammatory agent. Non-limiting examples of non-steroidal anti-inflammatory agents include choline salicylate, ibuprofen, ketoprofen, magnesium salicylate, meclofenamate sodium, naproxen sodium, and tolmetin sodium. In some implementations, the one or more anti-inflammatory substances is selected from a nonspecific anti-inflammatory such as ibuprofen and aspirin, or a COX-2 specific inhibitor such as rofecoxib and celecoxib.

In some embodiments, a therapeutic agent is an anti-cancer agent. In some embodiments, an anti-cancer agent is selected from an agent used in treating colorectal cancer. In some embodiments, the anti-cancer agent is selected from gemcitabine (Gemzar™), raltitrexed (Tomudex™) oxaliplatin (Eloxatin™), regorafenib, irinotecan (Camptostar™), and 5-fluorouracil (Adrucil™), and combinations thereof. In some embodiments, the anti-cancer agent is selected from capecitabine, fluorouracil, irinotecan and oxaliplatin, and combinations thereof.

In some embodiments, the anti-cancer agent is selected from an agent used in treating pancreatic cancer. In some embodiments, the anti-cancer agent is selected from gemcitabine (Gemzar™), fluorouracil (5-FU), irinotecan (Camptosar™), oxaliplatin (Eloxatin™), paclitaxel (Taxol™ or Abraxane™), capecitabine (Xeloda™) cisplatin, docetaxel (Taxotere™), and irinotecan (Onivyde™), and combinations thereof.

In some embodiments, the anti-cancer agent is selected from an agent used in treating lung cancer. In some embodiments, the anti-cancer agent is selected from cisplatin (Platinol™) carboplatin (Paraplatin™), docetaxel (Taxotere™), gemcitabine (Gemzar™), paclitaxel (Taxol™ and others), vinorelbine (Navelbine™ and others), pemetrexed (Alimta™), and combinations thereof.

In some embodiments, the anti-cancer agent is selected from an agent used in treating bone cancer. In some embodiments, the anti-cancer agent is selected from doxorubicin (Adriamycin®), cisplatin, etoposide (VP-16), ifosfamide (Ifex®), cyclophosphamide (Cytoxan®), methotrexate, and vincristine (Oncovin®), and combinations thereof.

In some embodiments, a therapeutic agent is a cell (e.g. a human cell). For example, the one or more therapeutic agents of a biomaterial can be selected from, pluripotent stem cells, multipotent stem cells, and induced pluripotent stem cells (iPSCs).

Methods of Printing Biomaterials.

Also disclosed herein are methods for printing biomaterials of the disclosure. In some embodiments, the biomaterials are printed using an extrusion-based process. Extrusion-based 3D printing can include any of: fused filament fabrication (FFF), fused deposition modeling (FDM), stereolithography, and gel mediums (with or without granules).

Printing of a biomaterial can comprise heating a polymer material the polymer's melting point and combining the polymer with a therapeutic agent, with or without additional ingredients, such as a porogen, to create a suspension of the therapeutic agent in the polymer material. The resulting combination, which is referred to here as a "slurry" can then loaded into a printing head of an extrusion-based 3D printer. The printing head can be, for example, a syringe. Variations of this process include, but are not limited to, combining the polymer material with the therapeutic agent and then heating the combination to the melting point of the polymer material to form the slurry. Additional ingredients, such as a porogen, can be added at any time during the process. The slurry is extruded onto a substrate along the pre-designed path to form a biomaterial as described herein using a layer by layer process. In some embodiments, the model for the biomaterial is obtained by computer aided design (CAD).

In some embodiments, biomaterials of the disclosure comprise multiple layers. Each layer can have a different geometry (e.g., staggered, slanted). Layered biomaterials can be constructed using a layer-by-layer process to achieve an overall mesh size of, for example, about 4× about 6 cm×about 0.5 cm (h×w×d).

In some embodiments, a biomaterial article as described herein is printed in layers using alternating layers of polymer material with and without the one or more therapeutic agents dispersed in the polymer. For example, (i) a first layer of polymer material containing a therapeutic agent dispersed in the polymer, (ii) a second layer of polymer material without the therapeutic agent, the second layer disposed on the first layer, and (iii) a third layer of polymer material containing the therapeutic agent dispersed in the polymer, the third layer disposed on the second layer. The layers are printed in this sequence, repeating until the article has attained a desired thickness. In some implementations, the article can have a thickness in the range of from 0.5 to 3.0 cm or from 0.5 to 2.0 cm, or from 0.5 to 1.0 cm.

Bioprinting Parameters.

A method disclosed herein can utilize a needle in a bioprinting process. In some embodiments, one or more polymeric materials, fugitive inks, ECM materials, cell suspensions, or a combination thereof is deposited through a needle onto a substrate. A method of the disclosure can print from more than one needle, for example, 1, 2, 3, 4, 5, 6, 7, 8, 9, 10, 11, 12, 13, 14, 15 or more needles. In some embodiments, a needle used in a method disclosed herein has a diameter that is expressed using the Birmingham gauge system. In some embodiments, a needle has a diameter of 7 gauge, 8 gauge, 9 gauge, 10 gauge, 11 gauge, 12 gauge, 13 gauge, 14 gauge, 15 gauge, 16 gauge, 17 gauge, 18 gauge, 19 gauge, 20 gauge, 21 gauge, 22 gauge, 22 s gauge, 23 gauge, 24 gauge, 25 gauge, 26 gauge, 26 s gauge, 27 gauge, 28 gauge, 29 gauge, 30 gauge, 31 gauge, 32 gauge, 33 gauge, or 34 gauge.

In some embodiments, a needle of the disclosure has a diameter of between 0.1 mm to 400 mm. In some embodiments, a needle of the disclosure has a diameter of between 0.1 mm to 0.5 mm, between 0.1 mm to 1 mm, between 0.1 mm to 10 mm, between 0.1 mm to 20 mm, between 0.1 mm to 30 mm, between 0.1 mm to 40 mm, between 0.1 mm to 50 mm, between 0.1 mm to 100 mm, between 0.1 mm to 200 mm, between 0.1 mm to 300 mm, between 0.1 mm to 400 mm, between 0.5 mm to 1 mm, between 0.5 mm to 10 mm, between 0.5 mm to 20 mm, between 0.5 mm to 30 mm, between 0.5 mm to 40 mm, between 0.5 mm to 50 mm, between 0.5 mm to 100 mm, between 0.5 mm to 200 mm, between 0.5 mm to 300 mm, between 0.5 mm to 400 mm, between 1 mm to 10 mm, between 1 mm to 20 mm, between 1 mm to 30 mm, between 1 mm to 40 mm, between 1 mm to 50 mm, between 1 mm to 100 mm, between 1 mm to 200 mm, between 1 mm to 300 mm, between 1 mm to 400 mm, between 10 mm to 20 mm, between 10 mm to 30 mm, between 10 mm to 40 mm, between 10 mm to 50 mm, between 10 mm to 100 mm, between 10 mm to 200 mm, between 10 mm to 300 mm, between 10 mm to 400 mm, between 20 mm to 30 mm, between 20 mm to 40 mm, between 20 mm to 50 mm, between 20 mm to 100 mm, between 20 mm to 200 mm, between 20 mm to 300 mm, between 20 mm to 400 mm, between 30 mm to 40 mm, between 30 mm to 50 mm, between 30 mm to 100 mm, between 30 mm to 200 mm, between 30 mm to 300 mm, between 30 mm to 400 mm, between 40 mm to 50 mm, between 40 mm to 100 mm, between 40 mm to 200 mm, between 40 mm to 300 mm, between 40 mm to 400 mm, between 50 mm to 100 mm, between 50 mm to 200 mm, between 50 mm to 300 mm, between 50 mm to 400 mm, between 100 mm to 200 mm, between 100 mm to 300 mm, between 100 mm to 400 mm, between 200 mm to 300 mm, between 200 mm to 400 mm, or between 300 mm to 400 mm. In some embodiments, a needle of the disclosure has a diameter of 0.1 mm, 0.2 mm, 0.5 mm, 1 mm, 10 mm, 20 mm, 30 mm, 40 mm, 50 mm, 100 mm, 200 mm, 300 mm, or 400 mm. In some embodiments, a needle of the disclosure has a diameter of at least 0.1 mm, at least 0.5 mm, at least 1 mm, at least 10 mm, at least 20 mm, at least 30 mm, at least 40 mm, at least 50 mm, at least 100 mm, at least 200 mm, or at least 300 mm. In some embodiments, a needle of the disclosure has a diameter of at most 0.5 mm, at most 1 mm, at most 10 mm, at most 20 mm, at most 30 mm, at most 40 mm, at most 50 mm, at most 100 mm, at most 200 mm, at most 300 mm, or at most 400 mm.

A method disclosed herein can comprise using an extruder to pass a material through a needle and onto a substrate. In some embodiments, multiple extruders deposit one or more materials onto a substrate. For example, multiple extruders can deposit material simultaneously, sequentially, or via a predefined sequence. In some embodiments, deposition from one or more extruders is controlled in real time. In some embodiments, printing is performed with 1, 2, 3, 4, 5, 6, 7, 8, 9, 10, 11, 12, 13, 14, 15, or more extruders.

The temperature at which an extruder operates can be controlled. In some embodiments, an extruder operates at a temperature of about 25° C. to about 200° C. In some embodiments, an extruder operates at a temperature of about 25° C. to about 37° C., about 25° C. to about 50° C., about 25° C. to about 75° C., about 25° C. to about 100° C., about 25° C. to about 150° C., about 25° C. to about 200° C., about 27° C. to about 37° C., about 27° C. to about 50° C., about 27° C. to about 75° C., about 27° C. to about 100° C., about 27° C. to about 150° C., about 27° C. to about 200° C., about 37° C. to about 50° C., about 37° C. to about 75° C., about 37° C. to about 100° C., about 37° C. to about 150° C., about 37° C. to about 200° C., about 50° C. to about 75° C., about 50° C. to about 100° C., about 50° C. to about 150° C., about 50° C. to about 200° C., about 75° C. to about 100° C., about 75° C. to about 150° C., about 75° C. to about 200° C., about 100° C. to about 150° C., about 100° C. to about 200° C., or about 150° C. to about 200° C. In some embodiments, an extruder operates at a temperature of about 25° C. about 27° C., about 37° C., about 50° C., about 65° C., about 75° C., about 100° C., about 150° C., or about 200° C. In some embodiments, an extruder operates at a temperature of at least about 25° C., at least about 27° C., at least about 37° C., at least about 50° C., at least about 75° C., at least about 100° C., or at least about 150° C. In some embodiments, an extruder operates at a temperature of at most about 25° C., at most about 37° C., at most about 50° C., at most about 75° C., at most about 100° C., at most about 150° C., or at most about 200° C.

In some embodiments, pressurized air is used to move a material through an extruder. The air pressure of an extruder can be controlled. In some embodiments, an extruder operates at an air pressure of about 600 kPa to about 800 kPa. In some embodiments, an extruder operates at an air pressure of about 600 kPa to about 625 kPa, about 600 kPa to about 650 kPa, about 600 kPa to about 675 kPa, about 600 kPa to about 700 kPa, about 600 kPa to about 725 kPa, about 600 kPa to about 750 kPa, about 600 kPa to about 775 kPa, about 600 kPa to about 800 kPa, about 625 kPa to about 650 kPa, about 625 kPa to about 675 kPa, about 625 kPa to about 700 kPa, about 625 kPa to about 725 kPa, about 625 kPa to about 750 kPa, about 625 kPa to about 775 kPa, about 625 kPa to about 800 kPa, about 650 kPa to about 675 kPa, about 650 kPa to about 700 kPa, about 650 kPa to about 725 kPa, about 650 kPa to about 750 kPa, about 650 kPa to about 775 kPa, about 650 kPa to about 800 kPa, about 675 kPa to about 700 kPa, about 675 kPa to about 725 kPa, about 675 kPa to about 750 kPa, about 675 kPa to about 775 kPa, about 675 kPa to about 800 kPa, about 700 kPa to about 725 kPa, about 700 kPa to about 750 kPa, about 700 kPa to about 775 kPa, about 700 kPa to about 800 kPa, about 725 kPa to about 750 kPa, about 725 kPa to about 775 kPa, about 725 kPa to about 800 kPa, about 750 kPa to about 775 kPa, about 750 kPa to about 800 kPa, or about 775 kPa to about 800 kPa. In some embodiments, an extruder operates at an air pressure of about 600 kPa, about 625 kPa, about 650 kPa, about 675 kPa, about 689.5 kPa, about 700 kPa, about 717.1 kPa, about 725 kPa, about 750 kPa, about 775 kPa, or about 800 kPa. In some embodiments, an extruder operates at an air pressure of at least about 600 kPa, at least about 625 kPa, at least about 650 kPa, at least about 675 kPa, at least about 700 kPa, at least about 725 kPa, at least about 750 kPa, or at least about 775 kPa. In some embodiments, an extruder operates at an air pressure of at most about 625 kPa, at most about 650 kPa, at most about 675 kPa, at most about 700 kPa, at most about 725 kPa, at most about 750 kPa, at most about 775 kPa, or at most about 800 kPa.

In some embodiments, an extruder operates at an air pressure of about 60 pounds per square inch (psi) to about 120 psi. In some embodiments, an extruder operates at an air pressure of about 87 psi to about 90.6 psi, about 87 psi to about 94.3 psi, about 87 psi to about 97.9 psi, about 87 psi to about 101.5 psi, about 87 psi to about 105.2 psi, about 87 psi to about 108.8 psi, about 87 psi to about 112.4 psi, about 87 psi to about 116 psi, about 90.6 psi to about 94.3 psi, about 90.6 psi to about 97.9 psi, about 90.6 psi to about 101.5 psi, about 90.6 psi to about 105.2 psi, about 90.6 psi to about 108.8 psi, about 90.6 psi to about 112.4 psi, about 90.6 psi to about 116 psi, about 94.3 psi to about 97.9 psi, about 94.3 psi to about 101.5 psi, about 94.3 psi to about 105.2 psi, about 94.3 psi to about 108.8 psi, about 94.3 psi to about 112.4 psi, about 94.3 psi to about 116 psi, about 97.9 psi to about 101.5 psi, about 97.9 psi to about 105.2 psi, about 97.9 psi to about 108.8 psi, about 97.9 psi to about 112.4 psi, about 97.9 psi to about 116 psi, about 101.5 psi to about 105.2 psi, about 101.5 psi to about 108.8 psi, about 101.5 psi to about 112.4 psi, about 101.5 psi to about 116 psi, about 105.2 psi to about 108.8 psi, about 105.2 psi to about 112.4 psi, about 105.2 psi to about 116 psi, about 108.8 psi to about 112.4 psi, about 108.8 psi to about 116 psi, or about 112.4 psi to about 116 psi. In some embodiments, an extruder operates at an air pressure of about 60 psi, about 87 psi, about 90.6 psi, about 94.3 psi, about 97.9 psi, about 100 psi, about 101.5 psi, about 104 psi, about 105.2 psi, about 108.8 psi, about 112.4 psi, about 116 psi, or about 120 psi. In some embodiments, an extruder operates at an air pressure of at least about 60 psi, at least about 87 psi, at least about 90.6 psi, at least about 94.3 psi, at least about 97.9 psi, at least about 101.5 psi, at least about 105.2 psi, at least about 108.8 psi, or at least about 112.4 psi. In some embodiments, an extruder operates at an air pressure of at most about 90.6 psi, at most about 94.3 psi, at most about 97.9 psi, at most about 101.5 psi, at most about 105.2 psi, at most about 108.8 psi, at most about 112.4 psi, at most about 116 psi, or at most about 120 psi.

A method of the disclosure can comprise printing a material at various linear extrusion speeds. In some embodiments, material is deposited at a linear extrusion speed of about 8 mm/s to about 800 mm/s. In some embodiments, material is deposited at a linear extrusion speed of about 100 mm/s to about 150 mm/s, about 100 mm/s to about 200 mm/s, about 100 mm/s to about 250 mm/s, about 100 mm/s to about 300 mm/s, about 100 mm/s to about 350 mm/s, about 100 mm/s to about 400 mm/s, about 100 mm/s to about 450 mm/s, about 100 mm/s to about 500 mm/s, about 100 mm/s to about 600 mm/s, about 100 mm/s to about 700 mm/s, about 100 mm/s to about 800 mm/s, about 150 mm/s to about 200 mm/s, about 150 mm/s to about 250 mm/s, about 150 mm/s to about 300 mm/s, about 150 mm/s to about 350 mm/s, about 150 mm/s to about 400 mm/s, about 150 mm/s to about 450 mm/s, about 150 mm/s to about 500 mm/s, about 150 mm/s to about 600 mm/s, about 150 mm/s to about 700 mm/s, about 150 mm/s to about 800 mm/s, about 200 mm/s to about 250 mm/s, about 200 mm/s to about 300 mm/s, about 200 mm/s to about 350 mm/s, about 200 mm/s to about 400 mm/s, about 200 mm/s to about 450 mm/s, about 200 mm/s to about 500 mm/s, about 200 mm/s to about 600 mm/s, about 200 mm/s to about 700 mm/s, about 200 mm/s to about 800 mm/s, about 250 mm/s to about 300 mm/s, about 250 mm/s to about 350 mm/s, about 250 mm/s to about 400 mm/s, about 250 mm/s to about 450 mm/s, about 250 mm/s to about 500 mm/s, about 250 mm/s to about 600 mm/s, about 250 mm/s to about 700 mm/s, about 250 mm/s to about 800 mm/s, about 300 mm/s to about 350 mm/s, about 300 mm/s to about 400 mm/s, about 300 mm/s to about 450 mm/s, about 300 mm/s to about 500 mm/s, about 300 mm/s to about 600 mm/s, about 300 mm/s to about 700 mm/s, about 300 mm/s to about 800 mm/s, about 350 mm/s to about 400 mm/s, about 350 mm/s to about 450 mm/s, about 350 mm/s to about 500 mm/s, about 350 mm/s to about 600 mm/s, about 350 mm/s to about 700 mm/s, about 350 mm/s to about 800 mm/s, about 400 mm/s to about 450 mm/s, about 400 mm/s to about 500 mm/s, about 400 mm/s to about 600 mm/s, about 400 mm/s to about 700 mm/s, about 400 mm/s to about 800 mm/s, about 450 mm/s to about 500 mm/s, about 450 mm/s to about 600 mm/s, about 450 mm/s to about 700 mm/s, about 450 mm/s to about 800 mm/s, about 500 mm/s to about 600 mm/s, about 500 mm/s to about 700 mm/s, about 500 mm/s to about 800 mm/s, about 600 mm/s to about 700 mm/s, about 600 mm/s to about 800 mm/s, or about 700 mm/s to about 800 mm/s. In some embodiments, material is deposited at a linear extrusion speed of about 8 mm/s, about 10 mm/s, about 100 mm/s, about 150 mm/s, about 200 mm/s, about 250 mm/s, about 300 mm/s, about 350 mm/s, about 400 mm/s, about 450 mm/s, about 500 mm/s, about 600 mm/s, about 700 mm/s, or about 800 mm/s. In some embodiments, material is deposited at a linear extrusion speed of at least about 8 mm/s, at least about 100 mm/s, at least about 150 mm/s, at least about 200 mm/s, at least about 250 mm/s, at least about 300 mm/s, at least about 350 mm/s, at least about 400 mm/s, at least about 450 mm/s, at least about 500 mm/s, at least about 600 mm/s, or at least about 700 mm/s. In some embodiments, material is deposited at a linear extrusion speed of at most about 150 mm/s, at most about 200 mm/s, at most about 250 mm/s, at most about 300 mm/s, at most about 350 mm/s, at most about 400 mm/s, at most about 450 mm/s, at most about 500 mm/s, at most about 600 mm/s, at most about 700 mm/s, or at most about 800 mm/s.

A method of the disclosure can comprise printing a material at various volumetric speeds. In some embodiments, the printing occurs with a volumetric speed of about 1 µL/s to about 100 µL/s. In some embodiments, the printing occurs with a volumetric speed of about 1 µL/s to about 5 µL/s, about 1 µL/s to about 10 µL/s, about 1 µL/s to about 15 µL/s, about 1 µL/s to about 20 µL/s, about 1 µL/s to about 25 µL/s, about 1 µL/s to about 50 µL/s, about 1 µL/s to about 100 µL/s, about 5 µL/s to about 10 µL/s, about 5 µL/s to about 15 µL/s, about 5 µL/s to about 20 µL/s, about 5 µL/s to about 25 µL/s, about 5 µL/s to about 50 µL/s, about 5 µL/s to about 100 µL/s, about 10 µL/s to about 15 µL/s, about 10 µL/s to about 20 µL/s, about 10 µL/s to about 25 µL/s, about 10 µL/s to about 50 µL/s, about 10 µL/s to about 100 µL/s, about 15 µL/s to about 20 µL/s, about 15 µL/s to about 25 µL/s, about 15 µL/s to about 50 µL/s, about 15 µL/s to about 100 µL/s, about 20 µL/s to about 25 µL/s, about 20 µL/s to about 50 µL/s, about 20 µL/s to about 100 µL/s, about 25 µL/s to about 50 µL/s, about 25 µL/s to about 100 µL/s, or about 50 µL/s to about 100 µL/s. In some embodiments, the printing occurs with a volumetric speed of about 1 µL/s, about 5 µL/s, about 10 µL/s, about 15 µL/s, about 20 µL/s, about 25 µL/s, about 50 µL/s, or about 100 µL/s. In some embodiments, the printing occurs with a volumetric speed of at least about 1 µL/s, at least about 5 µL/s, at least about 10 µL/s, at least about 15 µL/s, at least about 20 µL/s, at least about 25 µL/s, or at least about 50 µL/s. In some embodiments, the printing occurs with a volumetric speed of at most about 5 µL/s, at most about 10 µL/s, at most about 15 µL/s, at most about 20 µL/s, at most about 25 µL/s, at most about 50 µL/s, or at most about 100 µL/s.

A method of the disclosure can comprise controlling the deposition of materials (e.g. polymers) with a degree of resolution. In some embodiments, a method disclosed herein can control material deposition with a resolution of about 0.01 mm to about 1 mm. In some embodiments, a method disclosed herein can control material deposition with a resolution of about 0.01 mm to about 0.05 mm, about 0.01 mm to about 0.1 mm, about 0.01 mm to about 0.2 mm, about 0.01 mm to about 0.3 mm, about 0.01 mm to about 0.4 mm, about 0.01 mm to about 0.5 mm, about 0.01 mm to about 1 mm, about 0.05 mm to about 0.1 mm, about 0.05 mm to about 0.2 mm, about 0.05 mm to about 0.3 mm, about 0.05 mm to about 0.4 mm, about 0.05 mm to about 0.5 mm, about 0.05 mm to about 1 mm, about 0.1 mm to about 0.2 mm, about 0.1 mm to about 0.3 mm, about 0.1 mm to about 0.4 mm, about 0.1 mm to about 0.5 mm, about 0.1 mm to about 1 mm, about 0.2 mm to about 0.3 mm, about 0.2 mm to about 0.4 mm, about 0.2 mm to about 0.5 mm, about 0.2 mm to about 1 mm, about 0.3 mm to about 0.4 mm, about 0.3 mm to about 0.5 mm, about 0.3 mm to about 1 mm, about 0.4 mm to about 0.5 mm, about 0.4 mm to about 1 mm, or about 0.5 mm to about 1 mm. In some embodiments, a method disclosed herein can control material deposition with a resolution of about 0.01 mm, about 0.05 mm, about 0.1 mm, about 0.2 mm, about 0.3 mm, about 0.4 mm, about 0.5 mm, or about 1 mm. In some embodiments, a method disclosed herein can control material deposition with a resolution of at least about 0.01 mm, at least about 0.05 mm, at least about 0.1 mm, at least about 0.2 mm, at least about 0.3 mm, at least about 0.4 mm, or at least about 0.5 mm. In some embodiments, a method disclosed herein can control material deposition with a resolution of at most about 0.05 mm, at most about 0.1 mm, at most about 0.2 mm, at most about 0.3 mm, at most about 0.4 mm, at most about 0.5 mm, or at most about 1 mm.

Computer System

Bioprinting parameters such as, for example, deposition speed, extruder pressure, extruder temperature, extruder deposition patterns, the location of deposition, layer thickness, and the material deposited can be controlled by a computer system. In some embodiments, the computer system comprises a processor, a memory device, an operating system, and a software module for monitoring or operating the extruder. In some embodiments, the computer system comprises a digital processing device and includes one or more hardware central processing units (CPU). In further embodiments, the computer system includes an operating system configured to perform executable instructions. In some embodiments, the operating system is software, including programs and data, which manages the device's hardware and provides services for execution of applications. Suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. In some embodiments a mobile smart phone operating system is used. Non-limiting examples of mobile smart phone operating systems include Nokia® Symbian® OS, Apple® iOS®, Research In Motion® BlackBerry OS®, Google® Android®, Microsoft® Windows Phone® OS, Microsoft® Windows Mobile® OS, Linux, and Palm® WebOS. In some embodiments, the computer system includes a storage and/or memory device. In some embodiments, the storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the device is a storage device including, by way of non-limiting examples, CD-ROMs, DVDs, flash memory devices, magnetic disk drives, magnetic tapes drives, optical disk drives, and cloud computing-based storage. In some embodiments, the storage and/or memory device is a combination of devices such as those disclosed herein.

In some embodiments, the computer systems described herein include user interfaces. In further embodiments, the user interfaces include graphic user interfaces (GUIs), such as a Repetier-Host graphical user interface. In some embodiments, the user interfaces are interactive and present a user with menus and options for interacting with the computer systems and delivery systems described herein. In some embodiments, the computer system includes a display screen to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In some embodiments, an OLED display is a passive-matrix OLED (PMOLED) or active-matrix OLED (AMOLED) display. In some embodiments, the display is a plasma display. In some embodiments, the display is a video projector. In some embodiments, the display is a combination of displays such as those disclosed herein. In some embodiments, the device includes an input device to receive information from a user. In some embodiments, the input device is a keyboard. In some embodiments, the input device is a key pad. In some embodiments, the input device is the display screen, which is a touch screen or a multi-touch screen. In some embodiments, the input device is a microphone to capture voice or other sound input. In some embodiments, the systems, and software modules disclosed herein are intranet-based. In some embodiments, the systems and software modules are Internet-based. In some embodiments, the computer systems and software modules are World Wide Web-based. In some embodiments, the computer systems and software modules are cloud computing-based. In some embodiments, the computer systems and software modules are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof.

Methods of Use.

The biomaterials described herein can provide for the controlled and prolonged release of one or more therapeutic agents in situ at a target site in the body of a subject in need of treatment of a disease, disorder, or condition treatable by the one or more therapeutic agents. Release of the one or more therapeutic agents from the implanted article can occur through several mechanisms, including but not limited to diffusion through the polymer material, by transport through fluid-filled pores or channels in the polymer material, and through degradation of the polymer material.

Several structural features of a biomaterial disclosed herein can be adapted to modify the release of therapeutic agent(s) from the biomaterial. These structural features include but are not limited to the composition of the polymer material, the density and/or porosity of the polymer material, the sub-structure of the unit biomaterials (e.g. in a layered biomaterial) formed by the defined pattern of geometric elements, including the size, shape, and the number and arrangement of filled and open geometric elements.

The macro three-dimensional configuration of a biomaterial of the disclosure can also be adapted to modify release of therapeutic agent(s) and/or to focus release to a particular portion or region of the article. For example, a biomaterial can be folded or rolled for insertion into a target site. Several unit biomaterials can also be formed or printed into stacked layers having a desired orientation, including a staggered configuration. In some embodiments, the article can be coated with a coating. In some embodiments, the coating prevents a burst release upon placement of the biomaterial in situ. For example, the biomaterial can be coated with the same drug using a dip-coat method which is a standard method used in medicinal research and drug development. Dip coating of an article can be achieved by dipping the biomaterial into a polymer-drug solution and then drying the biomaterial to create a thin, uniform coating. Alternatively, a spray can be used to coat the biomaterial, which can allow for direct spraying of micro-droplets of a therapeutic agent onto the biomaterial itself. In some embodiments, a combination of the above can be used to coat the biomaterial using a hybrid method.

In some embodiments, a biomaterial releases one or more therapeutic agents over a period of time from about 1 day to about 1 week, about 1 week to about 1 month, about 1 month to about 2 months, about 2 months to about 6 months, about 6 months to about 12 months, about 12 months to about 24 months, about 24 months to about 42 months, about 24 months to about 54 months, or from about 24 months to about 60 months. In some embodiments, a biomaterial releases a therapeutic agent or agents over a period of time of about 24 months, about 30 months, about 36 months, about 42 months, about 54 months, or about 60 months. In some embodiments, a biomaterial releases a therapeutic agent or agents over a period of time of at least about 24 months, at least about 30 months, at least about 36 months, at least about 42 months, at least about 54 months, or at least about 60 months. In some embodiments, a biomaterial releases a therapeutic agent or agents over a period of time of at most about 24 months, at most about 30 months, at most about 36 months, at most about 42 months, at most about 54 months, or at most about 60 months.

Non-limiting examples of a subject include a human, primate, mouse, rat, dog, cat, cow, horse, goat, camel, sheep or a pig. In some embodiments, methods disclosed herein are methods of treating a subject in need thereof.

In some embodiments, a therapeutically effective amount of the one or more therapeutic agents can delivered to the in situ target site over a period of time, through implantation of a biomaterial of the disclosure.

Methods disclosed herein can treat conditions by, for example, alleviating, reducing, or reducing the likelihood of one or more symptoms or complications of a disease or disorder. In some embodiments, a method disclosed herein reduces the likelihood of a disease or disorder occurring in a subject. For example, in the context of cancer, treating the cancer can include slowing the growth of the cancer, slowing or preventing the occurrence of metastases, or further metastases, and promoting regression of one or more tumors in the subject being treated.

Methods of Treating Cancer.

The present disclosure provides methods of treating cancer in a subject in need thereof, the methods comprising implanting a biomaterial of the disclosure into a target site of the subject. In some embodiments, the target site is a portion of an organ, hard tissue, soft tissue, or lymph node. In some embodiments, the target site is a solid tumor or portion thereof. The surgical article can be loaded with an amount of one or more therapeutic agents effective to provide a therapeutic dose of the one or more agents to the target site in situ for a period of time ranging from weeks, to months, to years, as described supra.

In some embodiments, the subject in need of treatment is a human patient diagnosed with a cancer, for example, colorectal cancer, breast cancer, skin cancer, bone cancer, prostate cancer, liver cancer, lung cancer, brain cancer, cancer of the larynx, cancer of the gall bladder, pancreatic cancer, rectal cancer, parathyroid cancer, thyroid cancer, adrenal cancer, neural tissue cancer, head and neck cancer, colon cancer, stomach cancer, cancer of the bronchi, renal cancer, basal cell carcinoma, squamous cell carcinoma of both ulcerating and papillary type, metastatic skin carcinoma, osteosarcoma, Ewing's sarcoma, veticulum cell sarcoma, myeloma, giant cell tumor, small-cell lung tumor, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic comeal nerve tumor, marfanoid habitus tumor, Wilm's tumor, seminoma, ovarian tumor, cervical dysplasia and in situ carcinoma, neuroblastoma, retinoblastoma, soft tissue sarcoma, malignant carcinoid, mycosis fungoide, rhabdomyosarcoma, Kaposi's sarcoma, osteogenic and other sarcoma, renal cell tumor, polycythemia vera, adenocarcinoma, glioblastoma multiforma, leukemias, lymphomas, malignant melanomas, epidermoid carcinomas, carcinomas, sarcomas, hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, and nodular regenerative hyperplasia.

In embodiments, a biomaterial disclosed herein can be used to treat the subject is a having a malignant cancer or late-stage cancer. In some embodiments, the subject in need of treatment can also be one that is non-responsive or refractory to a currently available therapy, or to the standard of care therapy for the disease, disorder, or condition being treated, such as the cancer.

In some embodiments, a biomaterial disclosed herein can be used to treat a colorectal cancer, for example, a colon cancer, a rectal cancer, or a bowel cancer, or any cancer that developed in the colon or rectum. In some embodiments, a biomaterial for treating colon cancer comprises a therapeutic agent indicated for the treatment of colon cancer. In some embodiments, the biomaterial comprises a therapeutic agent selected from one or more of gemcitabine (Gemzar), raltitrexed (Tomudex™) oxaliplatin (Eloxatin™), regorafenib, irinotecan (Camptostar™), and 5-fluorouracil (Adrucil™). In some embodiments, the therapeutic agent is selected from capecitabine, fluorouracil, irinotecan and oxaliplatin, and combinations thereof.

In some embodiments, treating cancer according to the methods described herein leads to the elimination of a symptom or complication of the cancer being treated. Elimination of the symptom is not required. In some embodiments, the severity of the symptom is decreased. In the context of cancer, non-limiting examples of such symptoms include clinical markers of severity or progression including the degree to which a tumor secretes growth factors, degrades the extracellular matrix, becomes vascularized, loses adhesion to juxtaposed tissues, or metastasizes, as well as the number of metastases.

Treating cancer according to the methods described herein can result in a reduction in size of a tumor. A reduction in size of a tumor can also be referred to as tumor regression. In some embodiments, after treatment, tumor size is reduced by at least about 5% relative to the size of the tumor prior to treatment. In some embodiments, tumor size is reduced by at least about 10% after treatment. In some embodiments, tumor size is reduced by at least about 20% after treatment. In some embodiments, tumor size is reduced by at least about 30% after treatment. In some embodiments, tumor size is reduced by at least about 40% after treatment. In some embodiments, tumor size is reduced by at least about 50% after treatment. In some embodiments, tumor size is reduced by at least about 75% after treatment. In some embodiments, the size of a tumor can be measured as a diameter of the tumor.

Treating cancer according to the methods described herein can result in a reduction of tumor volume. In some embodiments, after treatment, tumor volume is reduced by at least about 5% relative to the size of the tumor prior to treatment. In some embodiments, tumor volume is reduced by at least about 10% after treatment. In some embodiments, tumor volume is reduced by at least about 20% after treatment. In some embodiments, tumor volume is reduced by at least about 30% after treatment. In some embodiments, tumor volume is reduced by at least about 40% after treatment. In some embodiments, tumor volume is reduced by at least about 50% after treatment. In some embodiments, tumor volume is reduced by at least about 75% after treatment.

Treating cancer according to the methods described herein can result in a decrease in number of tumors. Tumor number can be reduced by, for example, at least about 5%, at least about 10%, at least about 20%, at least about 30%, at least about 40%, at least about 50%, or at least about 75% relative to the number of tumors prior to treatment. Number of tumors can be measured by any reproducible measurement. The number of tumors can be measured by counting tumors visible to the naked eye or at a specified magnification (e.g. 2×, 3×, 4×, 5×, 10×, or 50× magnification).

Treating cancer according to the methods described herein can result in a decrease in number of metastatic lesions in tissues or organs other than the primary tumor site. Metastatic lesions can be reduced by, for example, at least about 5%, at least about 10%, at least about 20%, at least about 30%, at least about 40%, at least about 50%, or at least about 75% relative to the number of metastatic lesions prior to treatment. Number of metastatic lesions can be measured by any reproducible measurement. The number of tumors can be measured by counting tumors visible to the naked eye or at a specified magnification (e.g. 2×, 3×, 4×, 5×, 10×, or 50× magnification).

Treating cancer according to the methods described herein can result in an increase in average survival time of a population of treated subjects in comparison to a population receiving carrier alone. An increase in average survival time of a population can be measured by any reproducible methods. An increase in average survival time of a population can be measured, for example, by calculating for a population the average length of survival following initiation of treatment with an active compound (e.g. implantation of a biomaterial loaded with a therapeutic agent). An increase in average survival time of a population can also be measured, for example, by calculating for a population the average length of survival following completion of a first round of treatment with an active compound. In some embodiments, the average survival time of a population is increased by at least 30 days, at least 60 days, at least 90 days, or at least 120 days.

Treating cancer according to the methods described herein can result in increase in average survival time of a population of treated subjects in comparison to a population receiving the standard of care therapy. In some embodiments, the average survival time of a population is increased by at least 30 days, at least 60 days, at least 90 days, or at least 120 days. An increase in average survival time of a population can be measured by any reproducible methods. An increase in average survival time of a population may be measured, for example, by calculating for a population the average length of survival following initiation of treatment with an active compound (e.g. implantation of a biomaterial loaded with a therapeutic agent). An increase in average survival time of a population can also be measured, for example, by calculating for a population the average length of survival following completion of a first round of treatment with an active compound.

Treating cancer according to the methods described herein can result in a decrease in the mortality rate of a population of treated subjects in comparison to a population receiving carrier alone. Treating cancer according to the methods described herein can result in a decrease in the mortality rate of a population of treated subjects in comparison to an untreated population. Treating cancer according to the methods described herein can result in a decrease in the mortality rate of a population of treated subjects in comparison to a population receiving the standard of care therapy. For example, the mortality rate can be decreased by at least about 2%, at least about 5%, at least about 10% or at least about 25%. A decrease in the mortality rate of a population of treated subjects can be measured by any reproducible methods. A decrease in the mortality rate of a population can be measured, for example, by calculating for a population the average number of disease-related deaths per unit time following initiation of treatment with an active compound. A decrease in the mortality rate of a population can also be measured, for example, by calculating for a population the average number of disease-related deaths per unit time following completion of a first round of treatment with an active compound.

Treating cancer according to the methods described herein can result in a decrease in tumor growth rate. In some embodiments, a method disclosed herein reduces tumor growth rate by at least about 5%, at least about 10%, at least about 30%, at least about 40%, at least about 50%, or at least about 75% relative to number prior to treatment Tumor growth rate can be measured by any reproducible measurement. Tumor growth rate can be measured according to a change in tumor diameter per unit time. In some embodiments, after treatment the tumor growth rate can be about zero and is determined to maintain the same size, i.e., has stopped growing.

Treating a cancer according to the methods described herein can result in a decrease in tumor regrowth. In some embodiments, treatment with a method disclosed herein results in tumor regrowth that is at most about 5%, at most about 10%, at most about 20%, at most about 30%, at most about 40%, at most about 50%, or at most about 75%. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Methods of Treating Pain.

The disclosure also provides methods of treating or managing pain in a subject in need thereof, the method comprising implanting a biomaterial described here into a target site of the subject. In some embodiments, the target sites are nerves, connective tissue and skeletal muscle and tissue. The biomaterial can be loaded with an amount of the one or more therapeutic agents effective to provide a therapeutically-effective amount of the one or more agents to the target site in situ for a period of time ranging from weeks, to months, to years, as described above. In some embodiments, the subject in need is a human patient in need of treatment for postsurgical pain, peripheral nerve injury, or chronic lower back pain. In some embodiments, the subject is in need of treatment or management of pain associated with osteoarthritis, diabetic peripheral neuropathy or musculoskeletal injury or trauma.

In some embodiments, for treating pain described herein, one or more therapeutic agents of a biomaterial is an opioid. Non-limiting examples of opioids include morphine, fentanyl, hydromorphone, codeine, oxycodone, hydrocodone, tramadol, methadone, alfentanil, remifentanil, and derivations thereof.

In some embodiments of the methods for treating pain described herein, the one or more therapeutic agents is dexamethasone, ondansetron, acetaminophen, a nonsteroidal anti-inflammatory drug (NSAID), gabapentin, pregabalin, capsaicin, ketamine, memantine, clonidine, dexmedetomidine, tapentadol, transdermal fentanyl, a long acting local anesthetic, a cannabinoid, or a combination of any of the foregoing.

EXAMPLES

Example 1. Printing Process

A polymeric material, e.g., PCL or blended PCL/PLGA, and a therapeutic agent are mixed together and heated to the melting temperature of the polymeric material to form a slurry. A porogen, e.g., a bioactive glass, is mixed with the slurry and fed into a syringe fitted with a 20-30 gauge needle. Process parameters such as temperature, pressure and motion velocity are used to create meshes with a desired line width and height to produce a thickness of 1.0 cm. Each extruder is separately controlled via software, and features such as speed, size, and temperature are controlled individually. One extruder prints at 100° C. at a speed of 0.1 m/s on a 27 gauge needle whereas another prints at 27 degrees at a speed of 0.2 m/s on a 30 gauge needle. Other factors such as pressure are controlled for each individual extruder and are between 60 psi to 120 psi A petri dish is placed and the appropriate gauge and syringe type is placed into each extruder. The desired PSI, temperature, size, speed, and positioning is selected for each extruder. A mesh as described herein (e.g., PCL) is fabricated at 60° C. or 100° C. and is be molded into form at room temperature (25° C.) under warm water. The maximum temperature PCL withstands for printing without altering its composition is 160° C.

Example 2: Single Layer, PCL-Based Mesh Article

Figure 4A:
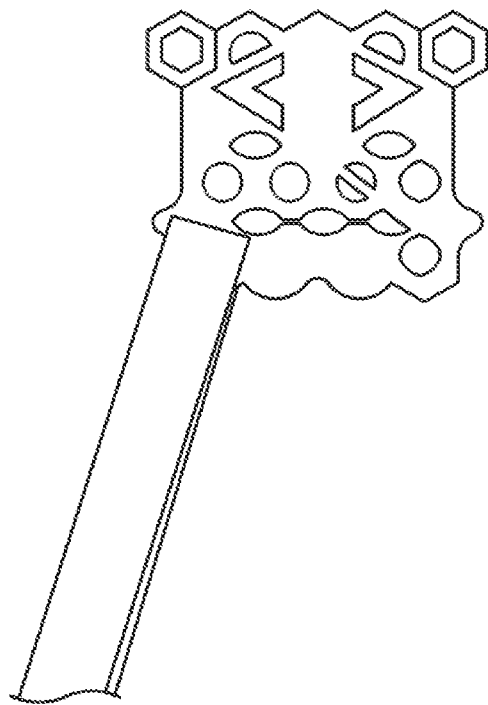
FIG. 4A shows a photograph of an approximately 1×1 cm 3-D printed, PCL-based surgical mesh of the disclosure.
Figure 4A:
Figure 4B:
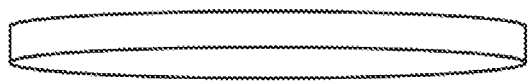
FIG. 4B shows a side view showing the thickness of the 1×1 cm 3-D-printed surgical mesh of FIG. 4A.
Figure 4B:
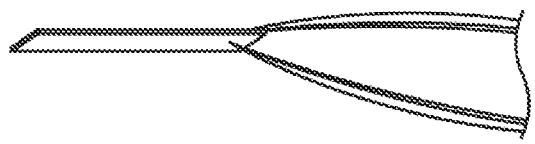

A single layer, PCL-based mesh biomaterial with dimensions of about 1 cm×1 cm was 3D printed at a temperature of 100.4° C. and a cartridge head pressure of 100.6 KPa. FIG. 4A shows a front view of the biomaterial and FIG. 4B shows the relative thickness of the biomaterial.

Example 3: Encapsulation Efficiency and Drug Release 5-fluorouracil and control biomaterials were printed out of 6,000 molecular weight PCL, through a thermoplastic printhead and a 0.3 mm steel nozzle. The nozzle temperature was 65° C., the bed temperature was 22° C., the print speed was 8 mm/s and the nozzle diameter was 0.2 mm. For biomaterials loaded with 5-fluorouracil, 5-fluorouracil was powdered using a mortal and pestle and blended with PCL. 5-fluorouracil was added at 30% weight compared to PCL.

5-fluoruracil loaded biomaterials were weighed and then dissolved in chloroform. 1 mL milliQ water was added and agitated by and vortex for 1 min, then incubated at room temperature overnight. Following the generation of a standard curve, the aqueous component was taken and read at 260 nm using a UV-Vis spectrophotometer to assess 5-fluorouracil (5-FU) content of biomaterials.

The following formula below was used to determine the encapsulation efficiency (EE) of the biomaterial, which was found to be ~4%:

EE (%)=([Amount of drug present in the final printed model (mg)]/[Amount of drug used in printing process (mg)])*100

Figure 5:
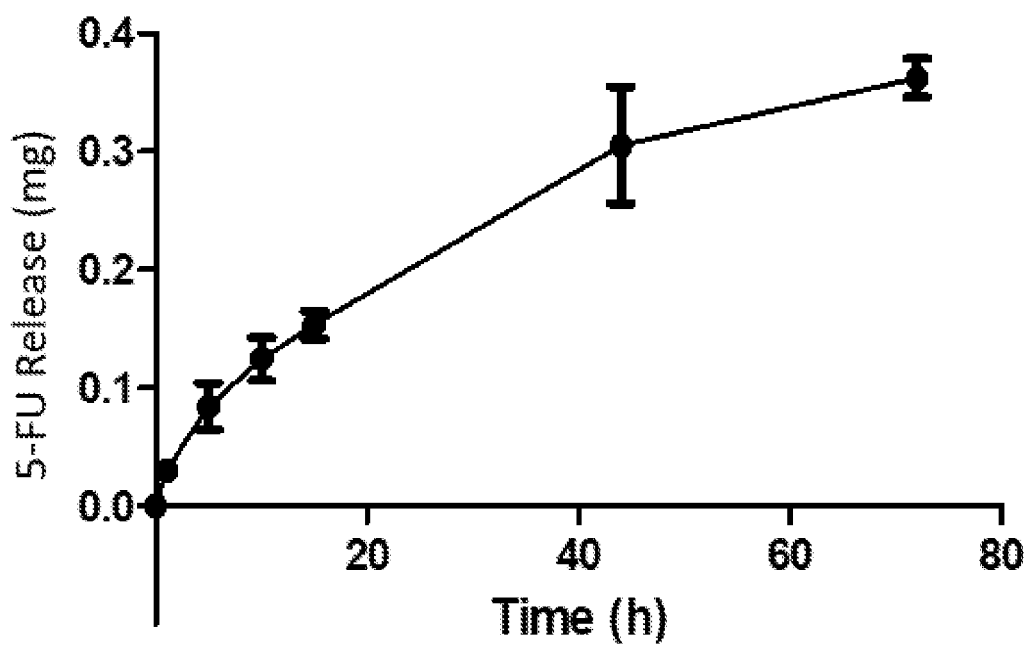
FIG. 5 shows a release profile of 5-fluorouracil (5-FU) from a biomaterial of the disclosure. Error bars represent standard deviation from three replicates.

To assess 5-FU release from printed biomaterials, biomaterials loaded with approximately 0.4 mg 5-FU were incubated in phosphate buffered saline at 37° C. and agitated with an electronic shaker. The amount of 5-FU released into solution was assessed via absorbance at 260 nm. The amount of 5-FU released from three biomaterials printed with the identical parameters is shown below in TABLE 1, as well as in FIG. 5.

TABLE 1

| Time (hrs.) | Sample 1 cumulative 5-FU release (mg) | Sample 2 cumulative 5-FU release (mg) | Sample 3 cumulative 5-FU release (mg) | Average cumulative 5-FU release (mg) | St. dev. |
|---|---|---|---|---|---|
| 0 | 0 | 0.001129667 | 0 | 0.000376556 | 0.001409068 |
| 1 | 0.025492817 | 0.038973509 | 0.024833845 | 0.029766724 | 0.007328507 |
| 5 | 0.101782991 | 0.089450794 | 0.062206993 | 0.084480259 | 0.019801341 |
| 10 | 0.142997006 | 0.146329524 | 0.083275281 | 0.124200604 | 0.017951886 |
| 15 | 0.173648636 | 0.18660215 | 0.100295596 | 0.153515461 | 0.011683652 |
| 44 | 0.375143562 | 0.338259936 | 0.202812871 | 0.305405456 | 0.049489234 |
| 72 | 0.44469339 | 0.400448101 | 0.241240374 | 0.362127288 | 0.016265312 |

EMBODIMENTS

The following non-limiting embodiments provide illustrative examples of the biomaterials and methods disclosed herein, but do not limit the scope of the disclosure.

Embodiment 1. A biomaterial comprising a first plurality of geometric elements and a therapeutically-effective amount of a therapeutic agent, wherein:
 a first geometric element of the first plurality of geometric elements is formed by a first porous border, wherein the first porous border comprises a polymer and the therapeutic agent;
 a second geometric element of the first plurality of geometric elements is formed by a non-porous border and a first solid region comprising the polymer, wherein the therapeutic agent cannot diffuse into the second geometric element;
 the first solid region is adjacent to and within the non-porous border; and
 a portion of the first porous border is adjacent to a portion of the non-porous border.

Embodiment 2. The biomaterial of embodiment 1, wherein the first geometric element comprises an empty space within the first porous border.

Embodiment 3. The biomaterial of embodiment 1, wherein the first geometric element is formed by the first porous border and a second solid region comprising the polymer, wherein the second solid region is adjacent to and within the first porous border.

Embodiment 4. The biomaterial of embodiment 3, wherein the second solid region has a degree of porosity that allows the therapeutic agent to diffuse into the second solid region from the first porous border.

Embodiment 5. The biomaterial of embodiment 4, wherein the degree of porosity is about 10% to about 90%.

Embodiment 6. The biomaterial of any one of embodiments 3-5, further comprising a third geometric element of the first plurality of geometric elements, wherein the third geometric element is formed by a second porous border comprising the polymer and the therapeutic agent, wherein a portion of the second porous border is adjacent to at least one of:
 a portion of the first porous border; and
 a portion of the non-porous border.

Embodiment 7. The biomaterial of embodiment 6, wherein geometric element comprises an empty space within the second porous border.

Embodiment 8. The biomaterial of embodiment 6, wherein the third geometric element is formed by the second porous border and a third solid region comprising the polymer and the therapeutic agent, wherein the third solid region is adjacent to and within the second porous border.

Embodiment 9. The biomaterial of embodiment 8, wherein the third solid region comprises the polymer with a degree of porosity of about 10% to about 90%.

Embodiment 10. The biomaterial of any one of embodiments 6-9, further comprising a fourth geometric element of the first plurality of geometric elements, wherein the fourth geometric element is formed by:
  (i) a third porous border comprising the polymer and the therapeutic agent; and
  (ii) a third solid region comprising the polymer;
wherein a portion of the third porous border is adjacent to at least one of:
  a portion of the first porous border;
  a portion of the second porous border; and
  a portion of the non-porous border,
  wherein the third solid region is adjacent to and within the third porous border.

Embodiment 11. The biomaterial of embodiment 10, wherein the third solid region further comprises the therapeutic agent.

Embodiment 12. The biomaterial of embodiment 10 or 11, wherein the third solid region has a degree of porosity of about 10% to about 90%.

Embodiment 13. The biomaterial of any one of embodiments 10-12, wherein the second solid region and the third solid region each have a degree of porosity, wherein the degree of porosity of the second solid region is different than the degree of porosity of the third solid region.

Embodiment 14. The biomaterial of any one of embodiments 1-13, wherein the first plurality of geometric elements forms a first layer.

Embodiment 15. The biomaterial of embodiment 14 wherein the biomaterial further comprises a second layer, wherein the second layer comprises a second plurality of geometric elements, wherein the second layer is in contact with the first layer and is layered onto the first layer.

Embodiment 16. The biomaterial of any one of embodiments 1-15, wherein the therapeutic agent is an anti-cancer agent.

Embodiment 17. The biomaterial of any one of embodiments 1-15, wherein the therapeutic agent is an anti-inflammatory agent.

Embodiment 18. The biomaterial of any one of embodiments 1-15 wherein the therapeutic agent is an antibiotic.

Embodiment 19. The biomaterial of any one of embodiments 1-15, wherein the therapeutic agent is an analgesic.

Embodiment 20. The biomaterial of any one of embodiments 1-15, wherein the therapeutic agent is 5-fluorouracil.

Embodiment 21. The biomaterial of any one of embodiments 1-20, wherein the polymer is polycaprolactone (PCL).

Embodiment 22. The biomaterial of any one of embodiments 1-20, wherein the polymer is poly lactic acid (PLA).

Embodiment 23. The biomaterial of any one of embodiments 1-20, wherein the polymer is poly L-lactide-glycolic acid (PLGA).

Embodiment 24. The biomaterial of any one of embodiments 1-20, wherein the polymer is polyethylene glycol diacrylate (PEGDA).

Embodiment 25. The biomaterial of any one of embodiments 1-24, wherein the first porous border further comprises a porogen.

Embodiment 26. The biomaterial of any one of embodiments 1-25, wherein the porogen is a bioactive glass.

Embodiment 27. The biomaterial of any one of embodiments 3-26, wherein the second solid region further comprises a porogen.

Embodiment 28. The biomaterial of embodiment 27, wherein the poragen is active glass.

Embodiment 29. The biomaterial of any one of embodiments 10-28, wherein the third solid region further comprises a porogen.

Embodiment 30. The biomaterial of embodiment 29 wherein the porogen is a bioactive glass.

Embodiment 31. The biomaterial of any one of embodiments 1-30, wherein the biomaterial is biodegradable.

Embodiment 32. A method of treating a condition, the method comprising implanting a biomaterial into a subject, wherein the biomaterial comprises a first plurality of geometric elements and a therapeutically-effective amount of a therapeutic agent, wherein:
  a first geometric element of the plurality of geometric elements is formed by a first porous border, wherein the first porous border comprises a polymer and the therapeutic agent;
  a second geometric element of the first plurality of geometric elements is formed by a non-porous border and a first solid region comprising the polymer, wherein the therapeutic agent cannot diffuse into the second geometric element from the first porous border;
  the first solid region is adjacent to and within the non-porous border; and
  a portion of the first porous border is adjacent to a portion of the non-porous border.

Embodiment 33. The method of embodiment 32, wherein the condition is cancer.

Embodiment 34. The method of embodiment 32, wherein the condition is colorectal cancer.

Embodiment 35. The method of embodiment 32, wherein the condition is pain.

Embodiment 36. The method of any one of embodiments 32-35, wherein the first geometric element comprises an empty space within the first porous border.

Embodiment 37. The method of any one of embodiments 32-35, wherein the first geometric element is formed by the first porous border and a second solid region comprising the polymer, wherein the second solid region is adjacent to and within the first porous border.

Embodiment 38. The method of embodiment 37, wherein the second solid region has a degree of porosity that allows the therapeutic agent to diffuse into the second solid region from the first porous border.

Embodiment 39. The method of embodiment 38, wherein the degree of porosity is about 10% to about 90%.

Embodiment 40. The method of embodiment 37 or 38, wherein the biomaterial further comprises a third geometric element of the first plurality of geometric elements, wherein the third geometric element is formed by a second porous border comprising the polymer and the therapeutic agent, wherein a portion of the second porous border is adjacent to at least one of
  a portion of the first porous border; and
  a portion of the non-porous border.

Embodiment 41. The method of embodiment 40, wherein the third geometric element comprises an empty space confined by the second porous border.

Embodiment 42. The method of embodiment 40, wherein the third geometric element is formed by the second porous border and a third solid region comprising the polymer and the therapeutic agent, wherein the third solid region is directly adjacent to and within a confine of the second porous border.

Embodiment 43. The method of any one of 40-42, wherein the third solid region comprises the polymer with a degree of porosity of about 10% to about 90%.

Embodiment 44. The method any one of embodiments 40-43, wherein the biomaterial further comprises a fourth geometric element of the first plurality of geometric elements, wherein the fourth geometric element is formed by:
 (i) a third porous border comprising the polymer and the therapeutic agent; and
 (ii) a third solid region comprising the polymer;
wherein a portion of the third porous border is adjacent to at least one of:
 a portion of the first porous border;
 a portion of the second porous border; and
 a portion of the non-porous border
wherein third solid region is adjacent to and within the third porous border.

Embodiment 45. The method of embodiment 44, wherein the third solid region further comprises the therapeutic agent.

Embodiment 46. The method of embodiment 44 or 45, wherein the third solid region has a degree of porosity of about 10% to about 90%.

Embodiment 47. The method of any one of embodiments 44-46, wherein the second solid region and the third solid region each have a degree of porosity, wherein the degree of porosity of the second solid region is different than the degree of porosity of the third solid region.

Embodiment 48. The method of any one of embodiments 32-47, wherein the first plurality of geometric elements forms a first layer.

Embodiment 49. The method of embodiment 48, wherein the biomaterial further comprises a second layer, wherein the second layer comprises a second plurality of geometric elements, wherein the second layer is in contact with the first layer and is layered onto the first layer.

Embodiment 50. The method of any one of embodiments 32-49, wherein the therapeutic agent is an anti-cancer agent.

Embodiment 51. The method of any one of embodiments 32-49, wherein the therapeutic agent is an anti-inflammatory agent.

Embodiment 52. The method of any one of embodiments 32-49, wherein the therapeutic agent is an antibiotic.

Embodiment 53. The method of any one of embodiments 32-49, wherein the therapeutic agent is an analgesic.

Embodiment 54. The method of any one of embodiments 32-49, wherein the therapeutic agent is 5-fluorouracil.

Embodiment 55. The method of any one of embodiments 32-54, wherein the polymer is polycaprolactone (PCL).

Embodiment 56. The method of any one of embodiments 32-54, wherein the polymer is poly lactic acid (PLA).

Embodiment 57. The method of any one of embodiments 32-54, wherein the polymer is poly L-lactide-glycolic acid (PLGA).

Embodiment 58. The method of any one of embodiments 32-54 wherein the polymer is polyethylene glycol diacrylate (PEGDA).

Embodiment 59. The method of any one of embodiments 32-58, wherein the first porous border further comprises a porogen.

Embodiment 60. The method of embodiment 59, wherein the porogen is a bioactive glass.

Embodiment 61. The method of any one of embodiments 37-60, wherein the second solid region further comprises a porogen.

Embodiment 62. The method of embodiment 61, wherein the porogen is a bioactive glass.

Embodiment 63. The method of any one of embodiments 44-62, wherein the third solid region further comprises a porogen.

Embodiment 64. The method of embodiment 63, wherein the porogen is a bioactive glass.

Embodiment 65. The method of any one of embodiments 32-64, wherein the biomaterial is biodegradable.

Embodiment 66. A method of treating a condition, the method comprising implanting a biomaterial into a subject, wherein the biomaterial comprises a polymer and a therapeutic agent, wherein, when in a controlled study in which the biomaterial is incubated in a solution of phosphate buffered saline at a temperature of 37° C. with agitation, the biomaterial:
 releases about 0.02 mg to about 0.04 mg of the therapeutic agent into the solution within 1 hour of commencement of the controlled study;
 releases about 0.07 mg to about 0.09 mg of the therapeutic agent into the solution within 5 hours of commencement of the controlled study;
 releases about 0.05 mg to about 0.15 mg of the therapeutic agent into the solution within 10 hours of commencement of the controlled study;
 releases about 0.1 mg to about 0.2 mg of the therapeutic agent into the solution within 15 hours of commencement of the controlled study;
 releases about 0.2 mg to about 0.4 mg of the therapeutic agent into the solution within 44 hours of commencement of the controlled study; and
 releases about 0.3 mg to about 0.5 mg of the therapeutic agent into the solution within 72 hours of commencement of the controlled study.

Embodiment 67. The method of embodiment 66, wherein in the controlled study, the biomaterial:
 releases about 0.03 mg of the therapeutic agent into the solution within 1 hour of commencement of the controlled study;
 releases about 0.08 mg of the therapeutic agent into the solution within 5 hours of commencement of the controlled study;
 releases about 0.12 mg of the therapeutic agent into the solution within 10 hours of commencement of the controlled study;
 releases about 0.15 mg of the therapeutic agent into the solution within 15 hours of commencement of the controlled study;
 releases about 0.31 mg of the therapeutic agent into the solution within 44 hours of commencement of the controlled study; and
 releases about 0.36 mg of the therapeutic agent into the solution within 72 hours of commencement of the controlled study.

What is claimed is:

1. A method of decreasing growth rate of a tumor having colorectal cancer cells in a subject, the method comprising implanting a biomaterial to a target site in the subject, wherein the target site comprises the tumor, wherein the tumor comprises the colorectal cancer cells, wherein the biomaterial comprises a first plurality of geometric elements and a therapeutically-effective amount of a therapeutic agent, wherein the therapeutic agent is 5-fluorouracil, wherein, upon the implanting, the therapeutically-effective amount of the therapeutic agent is released from the biomaterial at the target site, to effect a decrease in the growth rate of the tumor; and wherein:

a first geometric element of the first plurality of geometric elements is formed by a first porous border, wherein the first porous border comprises a polymer and the therapeutic agent;

a second geometric element of the first plurality of geometric elements is formed by a non-porous border and a first solid region comprising the polymer, wherein the therapeutic agent cannot diffuse into the second geometric element from the first porous border;

the first solid region is adjacent to and within the non-porous border; and a portion of the first porous border is adjacent to a portion of the non-porous border.

2. The method of claim 1, wherein the first geometric element comprises an empty space within the first porous border.

3. The method of claim 1, wherein the first geometric element is formed by the first porous border and a second solid region comprising the polymer, wherein the second solid region is adjacent to and within the first porous border.

4. The method of claim 3, wherein the second solid region has a degree of porosity that allows the therapeutic agent to diffuse into the second solid region from the first porous border.

5. The method of claim 3, wherein the biomaterial further comprises a third geometric element of the first plurality of geometric elements, wherein the third geometric element is formed by a second porous border comprising the polymer and the therapeutic agent, wherein a portion of the second porous border is adjacent to at least one of:

a portion of the first porous border; and a portion of the non-porous border.

6. The method of claim 5, wherein the third geometric element is formed by the second porous border and a third solid region comprising the polymer and the therapeutic agent, wherein the third solid region is directly adjacent to and within a confine of the second porous border.

7. The method of claim 5, wherein the biomaterial further comprises a fourth geometric element of the first plurality of geometric elements, wherein the fourth geometric element is formed by:

(i) a third porous border comprising the polymer and the therapeutic agent; and (ii) a third solid region comprising the polymer;

wherein a portion of the third porous border is adjacent to at least one of:

a portion of the first porous border;

a portion of the second porous border; and a portion of the non-porous border wherein third solid region is adjacent to and within the third porous border.

8. The method of claim 1, wherein the first plurality of geometric elements forms a first layer, and wherein the biomaterial further comprises a second layer, wherein the second layer comprises a second plurality of geometric elements, wherein the second layer is in contact with the first layer and is layered onto the first layer.

9. The method of claim 1, wherein the polymer is polycaprolactone (PCL).

10. The method of claim 1, wherein the polymer is poly lactic acid (PLA).

11. The method of claim 1, wherein the polymer is poly L-lactide-glycolic acid (PLGA).

12. The method of claim 1, wherein the polymer is polyethylene glycol diacrylate (PEGDA).

13. The method of claim 1, wherein the first porous border further comprises a porogen.

14. The method of claim 13, wherein the porogen is a bioactive glass.

15. The method of claim 1, wherein the biomaterial is biodegradable.

16. The method of claim 1, wherein the tumor is a solid tumor.

17. The method of claim 1, wherein the target site is adjacent to the tumor.

18. The method of claim 1, wherein the target site is a part of a gastrointestinal tract.

* * * * *